United States Patent
Lee et al.

(10) Patent No.: US 12,187,683 B2
(45) Date of Patent: Jan. 7, 2025

(54) BENZOINDAZOLONE COMPOUND AND INTERMEDIATE THEREOF

(71) Applicant: LMITO THERAPEUTICS INC., Yongin-si (KR)

(72) Inventors: Whee Seong Lee, Seongnam-si (KR); Eun Ju Lee, Suwon-si (KR); In Seok Ko, Pyoungtaek-si (KR)

(73) Assignee: LMITO THERAPEUTICS INC., Yongin-si (KR)

( * ) Notice: Subject to any disclaimer, the term of this patent is extended or adjusted under 35 U.S.C. 154(b) by 546 days.

(21) Appl. No.: 17/310,878

(22) PCT Filed: Feb. 20, 2020

(86) PCT No.: PCT/KR2020/002459
§ 371 (c)(1),
(2) Date: Aug. 27, 2021

(87) PCT Pub. No.: WO2020/175851
PCT Pub. Date: Sep. 3, 2020

(65) Prior Publication Data
US 2022/0144780 A1   May 12, 2022

(30) Foreign Application Priority Data

Feb. 28, 2019   (KR) ........................ 10-2019-0023942

(51) Int. Cl.
C07D 231/54   (2006.01)
C07D 405/12   (2006.01)

(52) U.S. Cl.
CPC ......... *C07D 231/54* (2013.01); *C07D 405/12* (2013.01)

(58) Field of Classification Search
CPC ............................ C07D 405/12; C07D 231/54
See application file for complete search history.

(56) References Cited

FOREIGN PATENT DOCUMENTS

| KR | 10-2008-0099174 A | 11/2008 |
|---|---|---|
| KR | 10-2015-0080423 A | 7/2015 |
| KR | 10-2016-0116296 A | 10/2016 |

OTHER PUBLICATIONS de Toledo et al., "Synthesis, Cytotoxicity and In Vitro Antileishmanial Activity of Naphthothiazoles", Chemical Biology & Drug Design, 2013, vol. 81, No. 6, pp. 749-756.
El-Aal et al., "Friedel-Crafts chemistry: Part 41. A new facile synthesis of indeno[1,2-c] pyrazoles, 2H-benzo[g] indazoles and benzo[6,7]cyclohepta[1,2-c]pyrazoles via Friedel-Crafts ring closures", European Journal of Chemistry, 2014, vol. 5, No. 2. pp. 277-286.
Geeraerts et al., "Macrophage Metabolism As Therapeutic Target for Cancer, Atherosclerosis, and Obesity", Frontiers in immunology, 2017, vol. 8, article 289, 13 pages.
Ginhoux et al., "New Insights Into The Multidimensional Concept of Macrophage Ontogeny, Activation and Function", Nature Immunology, 2016, vol. 17, No. 1, pp. 34-40.
Isidro et al., "Colonic macrophage polarization in homeostatis, inflammation, and cancer", Am J Physiol Gastrointest Liver Physiol, 2016, vol. 311, pp. G59-G73.
Langston et al., "Metabolism Supports Macrophage Activation", Frontiers in immunology, 2017, vol. 8, article 61, 7 pages.

*Primary Examiner* — Shawquia Jackson
(74) *Attorney, Agent, or Firm* — Vorys, Sater, Seymour and Pease LLP; Mih Suhn Koh

(57) ABSTRACT

Provided are a benzoindazolone compound, or a pharmaceutically acceptable salt, hydrate, solvate, enantiomer, diasteromer, tautomer or prodrug thereof; and an intermediate thereof, wherein the compound is used as a substrate for NQO1 to facilitate a redox reaction of NQO1, and thus is expected to be developable as a medicine for preventing or treating inflammatory diseases.

14 Claims, No Drawings

BENZOINDAZOLONE COMPOUND AND INTERMEDIATE THEREOF

TECHNICAL FILED

The present invention relates to a benzoindazolone compound and an intermediate thereof.

BACKGROUND ART

Our body's immune system has various defense systems to protect the body against internal stimuli or exterior pathogens. This immune system includes an immunity which increases an immune response, and an immune tolerance which regulates an excessive immune response. These two immune reactions are tightly regulated and maintain a balance of immunity and immune tolerance, which is called an immune homeostasis and is very important in maintaining optimal health.

However, the immune reactions may be dysfunctional due to the various internal or external factors. When the immunity is stronger than an immune tolerance, that is, when there are excessively activated immune cells around, inflammatory disorders or auto-immune diseases may occur. On the other hand, when the immune tolerance is stronger than immunity, that is, when the immune systems do not function properly, a body will get infectious diseases or cancers. Therefore, an ideal immunotherapy would be to enhance the homeostasis of immune system between immunity and immune tolerance and thereby to cure immune-related disorders.

Ulcerative colitis among inflammatory disorders is an inflammatory bowel disease (IBD) caused by genetic factors or excessive immune reactions, resulting in an inflammation or intestinal ulcer in colon. Its common symptoms are diarrhea containing mucus and blood, abdominal pain, weight loss, blood in stool, and the like. In many cases, IBD showed recurrent episodes of remission and induction, and may lead to colon cancer or to other complications. Despite many research in the area of IBD being performed, there is no therapy developed yet to cure the disease completely. Generally anti-inflammatory or adrenocortical hormone is being used in common, and depending on the disease condition of patients, immunosuppressive agents, steroids, antibiotics, or the like is used. There are several surgical treatments available; however, the complications of more problems after the surgery lead to suggest therapeutic treatment.

The autoimmune diseases have overly activated immune system resulting in attacking the host healthy cells and disrupt homeostasis. They include rheumatoid arthritis, Type 1 diabetes, inflammatory bowel disease, atopic dermatitis, and the like.

Our body possesses various immune suppressive cells to maintain immune homeostasis through inhibiting the auto-immune diseases or reducing overly activated immune responses, and macrophages among such cells play an important role in innate immunity and are present in many tissues in the body with various phenotypes.

Macrophages can protect our body from the attack of external pathogens through phagocytosis or secreting anti-microbial mediators. In addition, macrophages perform many diverse reactions such as wound healing as well as inflammatory responses. Macrophages can be categorized into two traditional phenotypes, M1 and M2 based on their pathological conditions. Instead of describing macrophage polarization dichotomically with M1 and M2, now it has been known as having diverse phenotypes based on their origins, places, microenvironment, and disease status (Nature Immunology 2016(17), 34; Am J Physiol Gastrointest Liver Physiol 2016(311), G59). Pro-inflammatory macrophages with M1 phenotype are activated by lipopolysaccharides (LPS) or by TNF-α□ and release IL-1β, IL-6, and TNF-α, and their major metabolic pathway is glycolysis in the cytosol, rather than mitochondrial metabolism. In contrast, the major metabolic pathway of M2-like macrophages is mitochondrial oxidative phosphorylation, and they are activated by IL-4 or IL-10 and play an important role in reducing inflammation and wound healing (Frontiers in immunology 2017, 61).

When NAD(P)H quinone oxidoreductase 1 (NQO1) enzyme is activated in the body, $NAD^+$ and $NAD^+/NADH$ ratio is increased, resulting in the activation of mitochondria, and therefore, the cell metabolism is converted from glycolysis to mitochondrial oxidative phosphorylation. This metabolic reprogramming induces macrophage polarization into anti-inflammatory M2 macrophages resulting in inhibition of expressions and activities of pro-inflammatory cytokines (Frontiers in immunology 2017, 289).

DETAILED DESCRIPTION OF THE INVENTION

Technical Problem to be Solved

An object of the present invention is to provide a novel benzoindazolone compound, or a pharmaceutically acceptable salt, hydrate, solvate, enantiomer, diasteromer, tautomer or prodrug thereof, which exhibits treatment effects against inflammatory diseases; and an intermediate thereof.

Technical Solution

The inventors have experimentally found that the novel benzoindazolone compound of the present invention is used as a substrate for NQO1 to facilitate a redox reaction of NQO1, and thus, it can be developed as a medicine for preventing or treating inflammatory diseases, by which the present invention has been completed.

Therefore, the first aspect of the present invention relates to a compound represented by the following Chemical Formula 1, or a pharmaceutically acceptable salt, hydrate, solvate, enantiomer, diasteromer, tautomer or prodrug thereof:

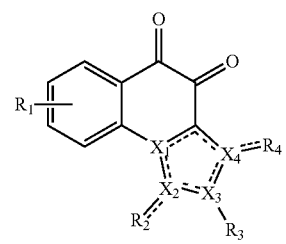

Chemical Formula 1 wherein, $R_1$ is selected from the group consisting of H, $C_{1-6}$ alkyl, $C_{1-6}$ alkoxy, substituted or unsubstituted $C_{6-10}$ aryl, substituted or unsubstituted heteroaryl, halo, cyano, nitro and $NR_5R_6$;

$R_2$ and $R_3$ are each independently not present, or selected from the group consisting of H, O, $C_{1-6}$ alkyl, substituted or unsubstituted $C_{6-10}$ aryl and $C_{1-6}$ alkoxy; and $R_4$ is selected from the group consisting of O, unsubstituted $C_{6-10}$ aryl and $C_{1-6}$ alkoxy, wherein at least one of $R_2$ and $R_4$ is/are O or $C_{1-6}$ alkoxy;

$R_5$ and $R_6$ are each independently H, $C_{1-6}$ alkyl or $C_{1-6}$ alkyl carbonyl, or $R_5$ and $R_6$ may be joined together to form a heterocyclyl containing at least one nitrogen atom in ring structure;

$X_1$, $X_2$, $X_3$ and $X_4$ are each independently selected from C and N, wherein two of $X_1$, $X_2$, $X_3$ and $X_4$ are N, provided that $X_2$ and $X_4$ cannot simultaneously be N, and $X_1$ and $X_4$ cannot simultaneously be N;

⸺ is a single bond or a double bond depending on $R_2$, $R_3$, $R_4$, $X_1$, $X_2$, $X_3$ and $X_4$;

wherein the alkyl is a linear, branched or cyclic alkyl, the heteroaryl is a 5- to 10-membered aromatic ring containing at least one hetero atom selected from the group consisting of N, O and S in the ring, wherein when the aryl or heteroaryl is substituted, a substituent thereof is $C_{1-6}$ alkyl, halo, or $C_{1-6}$ alkyl substituted with 1 to 3 halos.

The second aspect of the present invention relates to a compound, which is an intermediate for preparing the compound of Chemical Formula 1 as described above, represented by the following Chemical Formula 2:

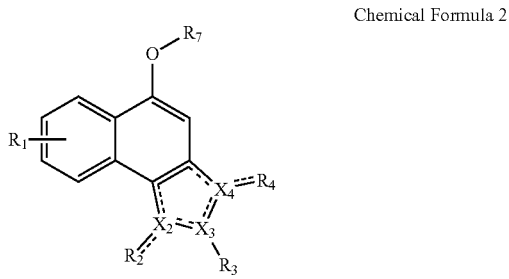

Chemical Formula 2 wherein, $R_1$, $R_2$, $R_3$, $R_4$, $X_2$, $X_3$, $X_4$ and ⸺ are the same as those defined for Chemical Formula 1, and $R_7$ is a typical protecting group for hydroxyl group which has been well known in the art.

Advantageous Effects

According to the prevent invention, a novel benzoindazolone compound and an intermediate for preparing the same were provided.

Through measurements of the amount of cytochrome C being reduced, it was found that the compound of the present invention was used as an effective substrate for NQO1. A redox reaction of NQO1 facilitated by the compound of the present invention can inhibit the expression and activities of inflammatory cytokines, and thus, the compound of the present invention is expected to be developed as a medicine for preventing or treating inflammatory diseases.

DETAILED DESCRIPTION OF THE EMBODIMENTS

Definition of Terms

The terms used in the present disclosure are briefly defined herein.

The term "pharmaceutically acceptable salt" means a salt form of a compound which does not cause any serious stimuli in an organism to which the compound is administered, and does not destroy biological activities and physical properties of the compound.

The terms "hydrate", "solvate", "prodrug", "tautomer", "enantiomer" and "diastereomer" also mean forms of a compound which does not cause any serious stimuli in an organism to which the compound is administered, and does not destroy biological activities and physical properties of the compound.

The pharmaceutically acceptable salt includes an acid-adduct salt which is formed by addition of an inorganic acid, such as hydrochloric acid, sulfuric acid, nitric acid, phosphoric acid, hydrobromic acid, hydriodic acid and the like, or an organic acid, such as tartaric acid, formic acid, citric acid, acetic acid, trichloroacetic acid, fluoroacetic acid, gluconic acid, benzoic acid, lactic acid, fumaric acid, maleic acid, salicylic acid, methanesulfonic acid, ethanesulfonic acid, benzenesulfonic acid, p-toluenesulfonic acid and the like.

In case that a carboxyl acid group is present in the compound of Chemical Formula 1 above, an example of a pharmaceutically acceptable carboxylic acid salt includes a metal salt or an alkaline earth metal salt formed with lithium, sodium, potassium, calcium, magnesium or the like; an amino acid salt formed with lysine, arginine, guanidine or the like; and an organic salt formed with dicyclohexylamine, N-methyl-D-glucamine, tris(hydroxymethyl)methylamine, diethanolamine, choline, trimethylamine or the like. The compound of Chemical Formula 1 according to the present invention may be converted into its salt by a conventional method.

The term "hydrate" means a compound according to the present invention containing a stoichiometric or non-stoichiometric amount of water bound through non-covalent intermolecular forces, or a salt thereof.

The term "solvate" means a compound according to the present invention containing a stoichiometric or non-stoichiometric amount of solvent bound through non-covalent intermolecular forces, or a salt thereof. A solvent for the solvate may be any solvent which is volatile, non-toxic and/or suitable for administration to a human.

The term "prodrug" means a substance which can be converted in vivo into the compound of Chemical Formula 1 according to the present invention. In some cases, a prodrug is often used because it may be more easily administered than its parent drug. For example, biological activities can be achieved by oral administration of a prodrug, while it is not possible with its parent drug. In addition, a prodrug may have better solubility compared with its parent drug in a pharmaceutical formulation. For example, a prodrug may be in the form of an ester (a "prodrug"), which is easy to pass through cell membrane and can be hydrolyzed by a metabolism into a carboxylic acid as an active form within a cell where its water solubility is beneficial, although its water solubility is disadvantageous for transportation. Another example of the prodrug may be a short peptide (a poly-amino acid), in which a peptide is linked to an acid group, which is metabolized so that its active site is exposed.

The term "tautomer" means a type of structural isomers having an identical chemical or molecular formula, but different coupling between constituent atoms. For example, its structure is converted into each other between both isomers, such as a keto-enol structure.

The term "enantiomer" or "diastereomer" means an isomer which occurs due to different arrangements of atoms in a molecule even having an identical chemical formula or molecular formula. The term "enantiomer" means an isomer which is not superimposed with its mirror image, like a relation between a right hand and a left hand. In addition, the term "diastereomer" means a stereoisomer which is not in a mirror image relation. All isomers and mixtures thereof are also within the scope of the present invention.

The term "alkyl" means an aliphatic hydrocarbon group, which includes "saturated alkyl," and "unsaturated alkyl" containing at least one double bond or triple bond, and includes a linear, branched and cyclic alkyl.

The term "heterocyclyl" means a 3- to 7-membered cyclic group having at least one hetero atom selected from the group consisting of nitrogen (N), oxygen (O) and sulfur (S) in the cycle, and the term "heteroaryl" means a 5- to 10-membered aromatic ring at least one hetero atom selected from the group consisting of nitrogen (N), oxygen (O) and sulfur (S) in the ring.

Hereinafter, the present invention will be described in more detail.

The first aspect of the present invention relates to a compound represented by the following Chemical Formula 1, or a pharmaceutically acceptable salt, hydrate, solvate, enantiomer, diastereomer, tautomer or prodrug thereof:

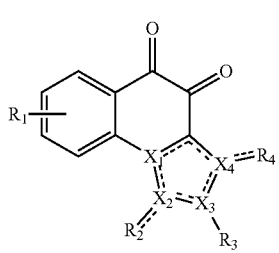

Chemical Formula 1 wherein, $R_1$ is selected from the group consisting of H, $C_{1-6}$ alkyl, $C_{1-6}$ alkoxy, substituted or unsubstituted $C_{6-10}$ aryl, substituted or unsubstituted heteroaryl, halo, cyano, nitro and $NR_5R_6$;

$R_2$ and $R_3$ are each independently not present, or selected from the group consisting of H, O, $C_{1-6}$ alkyl, substituted or unsubstituted $C_{6-10}$ aryl and $C_{1-6}$ alkoxy; and $R_4$ is selected from the group consisting of O, unsubstituted $C_{6-10}$ aryl and $C_{1-6}$ alkoxy, wherein at least one of $R_2$ and $R_4$ are O or $C_{1-6}$ alkoxy;

$R_5$ and $R_6$ are each independently H, $C_{1-6}$ alkyl or $C_{1-6}$ alkyl carbonyl, or $R_5$ and $R_6$ may be joined together to form a heterocyclyl containing at least one nitrogen atom in ring structure;

$X_1$, $X_2$, $X_3$ and $X_4$ are each independently selected from C and N, wherein two of $X_1$, $X_2$, $X_3$ and $X_4$ are N, provided that $X_2$ and $X_4$ cannot simultaneously be N, and $X_1$ and $X_4$ cannot simultaneously be N;

⸻ is a single bond or a double bond depending on $R_2$, $R_3$, $R_4$, $X_1$, $X_2$, $X_3$ and $X_4$;

wherein the alkyl is a linear, branched or cyclic alkyl, the heteroaryl is a 5- to 10-membered aromatic ring containing at least one hetero atom selected from the group consisting of N, O and S in the ring, wherein when the aryl or heteroaryl is substituted, a substituent thereof is $C_{1-6}$ alkyl, halo, or $C_{1-6}$ alkyl substituted with 1 to 3 halos.

In one embodiment of the compound of Chemical Formula 1 of the present invention, at least one of $R_2$, $R_3$ and $R_4$ may be $C_{1-6}$ alkoxy, wherein an alkyl consisting of the alkoxy is a linear, branched or cyclic alkyl.

In another embodiment of the compound of Chemical Formula 1 of the present invention, at least one of bonds between $R_2$ and $X_2$, $R_3$ and $X_3$, and $R_4$ and $X_4$ may be C=O.

In still another embodiment of the compound of Chemical Formula 1 of the present invention, at least two of ⸻ may be double bond.

In still another embodiment of the compound of Chemical Formula 1 of the present invention, $X_1$ and $X_4$ may be C, and $X_2$ and $X_3$ may be N. Herein, $R_4$ may be $C_{1-6}$ alkoxy, or the bond between $R_4$ and $X_4$ may be C=O.

In still another embodiment of the compound of Chemical Formula 1 of the present invention, $X_1$ and $X_2$ may be C, and $X_3$ and $X_4$ may be N. Herein, $R_2$ may be $C_{1-6}$ alkoxy, or the bond between $R_2$ and $X_2$ may be C=O.

In still another embodiment of the compound of Chemical Formula 1 of the present invention, $X_2$ and $X_3$ may be C, and $X_1$ and $X_3$ may be N. Herein, $R_2$ may be $C_{1-6}$ alkyl-substituted or unsubstituted aryl.

In the compound of Chemical Formula 1, the halo is any of fluoro, chloro, bromo and iodo.

The compound of Chemical Formula 1 according to the present invention includes the following Compounds 1 to 25:

Compound 1: 1-phenyl-1H-benzo[g]indazol-3,4,5(2H)-trione;
Compound 2: 3-isopropoxy-1-phenyl-1H-benzo[g]indazol-4,5-dione;
Compound 3: 2-isopropyl-1-methyl-1H-benzo[g]indazol-3,4,5(2H)-trione;
Compound 4: 2-isopropyl-3-methoxy-2H-benzo[g]indazole-4,5-dione;
Compound 5: 2-methyl-1-phenyl-1H-benzo[g]indazole-3,4,5 (2H)-trione;
Compound 6: 3-methoxy-1-phenyl-1H-benzo[g]indazol-4,5-dione;
Compound 7: 2-ethyl-1-phenyl-1H-benzo[g]indazol-3,4,5 (2H)-trione;
Compound 8: 3-ethoxy-1-phenyl-1H-benzo[g]indazol-4,5-dione;
Compound 9: 2-isobutyl-1-phenyl-1H-benzo[g]indazol-3,4,5(2H)-trione;
Compound 10: 3-isobutoxy-1-phenyl-1H-benzo[g]indazol-4,5-dione;
Compound 11: 2-isopentyl-1-phenyl-1H-benzo[g]indazol-3,4,5(2H)-trione;
Compound 12: 3-(isopentyloxy)-1-phenyl-1H-benzo[g]indazol-4,5-dione;
Compound 13: 2-isopropyl-1-phenyl-1H-benzo[g]indazol-3,4,5(2H)-trione;
Compound 14: 2-methyl-3-phenyl-2,3-dihydro-1H-benzo[e]indazol-1,4,5-trione;
Compound 15: 1-methoxy-3-phenyl-3H-benzo[e]indazol-4,5-dione;
Compound 16: 1-isopropyl-2-methyl-1H-benzo[g]indazol-3,4,5(2H)-trione;
Compound 17: 1-isopropyl-3-methoxy-1H-benzo[g]indazol-4,5-dione;
Compound 18: 3-methoxy-1-(4-(trifluoromethyl)phenyl)-1H-benzo[g]indazol-4,5-dione;
Compound 19: 1-(4-fluorophenyl)-3-methoxy-1H-benzo[g]indazol-4,5-dione;
Compound 20: 1-methyl-2-phenyl-1H-benzo[g]indazol-3,4,5 (2H)-trione;
Compound 21: 7-fluoro-2-methyl-1-phenyl-1H-benzo[g]indazol-3,4,5(2H)-trione;
Compound 22: 7-fluoro-3-methoxy-1-phenyl-1H-benzo[g]indazol-4,5-dione;

Compound 23: 3-methoxy-7-nitro-1-phenyl-1H-benzo[g]indazol-4,5-dione;
Compound 24: 7-amino-3-methoxy-1-phenyl-1H-benzo[g]indazol-4,5-dione; and
Compound 25: 7-bromo-3-methoxy-1-phenyl-1H-benzo[g]indazol-4,5-dione.

The second aspect of the present invention relates to a compound, which is an intermediate for preparing the compound of Chemical Formula 1 as described above, represented by the following Chemical Formula 2:

Chemical Formula 2

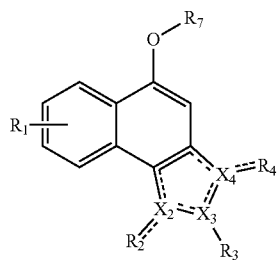

wherein, $R_1$, $R_2$, $R_3$, $R_4$, $X_2$, $X_3$, $X_4$ and ═══ are the same as those defined for Chemical Formula 1, and $R_7$ is a typical protecting group for hydroxyl group which has been well known in the art. Examples of the protecting group include $C_{1-6}$ alkyl; $C_{6-10}$ aryl-substituted $C_{1-6}$ alkyl, such as benzyl, trityl, methoxybenzyl and the like; $C_{1-6}$ alkoxy-substituted $C_{1-6}$ alkyl, such as methoxymethyl, methoxyethoxymethyl and the like; 5- to 6-membered heterocyclyl containing at least one hetero atom, such as tetrahydropyranyl, tetrahydrofuranyl and the like; $C_{1-6}$ alkyl-substituted silyl, such as trimethylsilyl, triisopropylsilyl, t-butyldimethylsilyl and the like; $C_{1-6}$ alkyl carbonyl, such as acetyl, pivaloyl and the like, but not limited thereto.

The compound of Chemical Formula 2 may be selected from the group consisting of the following:
5-methoxy-1-phenyl-1H-benzo[g]indazol-3(2H)-one;
2-isopropyl-5-methoxy-1H-benzo[g]indazol-3(2H)-one;
5-methoxy-3-phenyl-2,3-dihydro-1H-benzo[e]indazol-1-one;
1-isopropyl-5-methoxy-1H-benzo[g]indazol-3(2H)-one;
5-methoxy-1-(4-(trifluoromethyl)phenyl)-1H-benzo[g]indazol-3(2H)-one;
1-(4-fluorophenyl)-5-methoxy-1H-benzo[g]indazol-3(2H)-one;
5-methoxy-2-phenyl-1H-benzo[g]indazol-3(2H)-one;
7-fluoro-5-methoxy-1-phenyl-1H-benzo[g]indazol-3(2H)-one;
5-methoxy-7-nitro-1-phenyl-1H-benzo[g]indazol-3(2H)-one;
7-bromo-5-methoxy-1-phenyl-1H-benzo[g]indazol-3(2H)-one;
5-(benzyloxy)-1-phenyl-1,2-dihydro-3H-benzo[g]indazol-3-one;
5-(methoxymethoxy)-1-phenyl-1,2-dihydro-3H-benzo[g]indazol-3-one;
1-phenyl-5-((tetrahydro-2H-pyran-2-yl)oxy)-1,2-dihydro-3H-benzo[g]indazol-3-one;
1-phenyl-5-((trimethylsilyl)oxy)-1,2-dihydro-3H-benzo[g]indazol-3-one; and
3-oxo-1-phenyl-2,3-dihydro-1H-benzo[g]indazol-5-yl acetate.

The third aspect of the present invention relates to a pharmaceutical composition comprising as an active ingredient the compound of Chemical Formula 1, or a pharmaceutically acceptable salt, hydrate, solvate, enantiomer, diastereomer, tautomer or prodrug thereof.

The pharmaceutical composition may further comprise at least one component selected from the group consisting of a carrier, an excipient and a diluent, which have been well known in the art.

The compound of Chemical Formula 1 according to the present invention is used as a substrate for NQO1, by which it can inhibit expressions and activities of inflammatory cytokines, and thus, it can be used for prevention or treatment of diseases which relate to NQO1 activities.

EXAMPLES

Hereinafter, the present invention will be described in more detail with reference to examples. However, the examples are provided only for illustration of the present invention, and should not be construed as limiting the scope of the present invention.

Preparation Example 1: Synthesis of Intermediate 1 (1-bromo-4-methoxy-2-naphthoic acid)

(1) Synthesis of methyl 1-hydroxy-3-naphthoate

Benzaldehyde (282 mmol) and dimethyl succinate (310.2 mmol) were put into a round bottom flask, and dissolved in methanol (100 mL). When the reactants were well dissolved, 25% Sodium methoxide solution (366.6 mmol) was slowly added, and reaction mixture was stirred under reflux for 12 hours. The reaction mixture was acidified with 3M HCl to pH 1, transferred to a separatory funnel, and then extracted three times with dichloromethane. Combined organic layer was dried over $MgSO_4$ and concentrated under reduced pressure to give crude product. The crude product was dissolved in THF (80 mL), to which trifluoroacetic anhydride (282 mmol) was slowly added, and the reaction mixture was stirred under reflux until the completion of the reaction was observed. After confirming the completion of the reaction with TLC, the reaction mixture was cooled to room temperature, moved into an ice bath, and then neutralized to pH 7-8 with slow addition of sat. aq. $NaHCO_3$ solution. When neutralization was completed, the reaction mixture was extracted three times with ethyl acetate, and combined organic layer was dried over $MgSO_4$ and concentrated under reduced pressure. The crude product was recrystallized with ethyl acetate and n-hexane, and mother liquor was purified by column chromatography.

Yellowish solid, Yield: 30%

$^1$H NMR (300 MHz, $CDCl_3$) δ: 8.26-8.21 (m, 2H), 7.93-7.90 (m, 1H), 7.63-7.51 (m, 3H), 5.95 (s, 1H), 3.98 (s, 3H).

(2) Synthesis of methyl 4-methoxy-2-naphthoate

Methyl 1-hydroxy-3-naphthoate (4.54 mmol) and $K_2CO_3$ (9.08 mmol) were put into a round bottom flask and dissolved in anhydrous DMF (15 mL). Methyl iodide (9.54 mmol) was added and then the reaction mixture was stirred at room temperature for 2 hours. The reaction mixture was transferred to a separatory funnel, to which water was added, and then extracted three times with dichloromethane. Combined organic layer was dried over $MgSO_4$ and concentrated under reduced pressure. The crude product was used for the next step without further purification.

(3) Synthesis of methyl 1-bromo-4-methoxy-2-naphthoate

Methyl-1-hydroxy-3-naphthoate (24.7 mmol) was put into a round bottom flask and dissolved in acetonitrile (60 mL), to which N-bromosuccinimide (23.7 mmol) was added portion-wise over 2 minutes. The reaction mixture was stirred for 60 hours. The solvent was removed under reduced pressure. The crude mixture was dissolved in ethyl acetate, transferred to a separatory funnel, and then washed with saturated aq. NaHCO$_3$ solution twice. Organic layer was dried over MgSO$_4$ and concentrated under reduced pressure. The crude product was recrystallized with ethyl acetate and n-hexane, and mother liquor was purified by column chromatography.

Yellowish solid, Yield: 90%.

$^1$H NMR (300 MHz, CDCl$_3$) δ: 8.42 (d, J=8.3 Hz, 1H), 8.30 (d, J=7.7 Hz, 1H), 7.70-7.59 (m, 2H), 7.05 (s, 1H), 4.05 (s, 3H), 4.03 (s, 3H).

(4) Synthesis of Intermediate 1 (1-bromo-4-methoxy-2-naphthoic acid)

Methyl 1-bromo-4-methoxy-2-naphthoate (17.8 mmol, 5) was put into a round bottom flask and dissolved in THF, methanol and water (1:1:1 v/v). When sufficiently dissolved, KOH (53.4 mmol) was added, and then the reaction mixture was stirred under reflux for 3 hours. The reaction mixture was cooled to room temperature, transferred to a separatory funnel, and then acidified with 3M HCl to pH 1. The mixture was extracted four times with ethyl acetate, and combined organic layer was dried over MgSO$_4$. The solvent was removed under reduced pressure. The crude product was recrystallized from dichloromethane.

White solid, Yield: 99%.

$^1$H NMR (300 MHz, CDCl$_3$) δ: 8.48 (d, J=7.9 Hz, 1H), 8.31 (d, J=8.0 Hz, 1H), 7.72-7.60 (m, 2H), 7.25 (s, 1H), 4.06 (s, 3H).

Preparation Example 2: Synthesis of Intermediate 2 (5-methoxy-1-phenyl-1H-benzo[g]indazol-3(2H)-one)

(1) Synthesis of 1-bromo-4-methoxy-N'-phenyl-2-naphthohydrazide

1-Bromo-4-methoxy-2-naphthoic acid (7.2 mmol, Intermediate 1) and phenyl hydrazine hydrochloride (8.64 mmol) were put into a round bottom flask and dissolved in dichloromethane (72 mL). To the reaction mixture, triethylamine (21.3 mmol) was added. When it is observed that the color of the reaction solution becomes transparent after stirring at room temperature for 5 minutes, bis(2-oxo-3-oxazolidinyl) phosphinic chloride (8.64 mmol) was added. The reaction mixture was stirred at room temperature for 6 hours. The reaction was quenched with addition of sat. aq. NaHCO$_3$ solution, and the reaction mixture was transferred to a separatory funnel and extracted three times with dichloromethane. Combined organic layer was dried over MgSO$_4$ and concentrated under reduced pressure. The crude product was recrystallized with ethyl acetate and n-hexane.

Yellowish white solid, Yield: 80%

$^1$H NMR (300 MHz, DMSO-d$_6$) δ: 10.23 (s, 1H), 8.26-8.23 (m, 2H), 7.97 (s, 1H), 7.81-7.67 (m, 2H), 7.22-7.17 (m, 2H), 6.97-6.93 (m, 3H), 6.77-6.72 (m, 1H), 4.05 (s, 3H).

(2) Synthesis of Intermediate 2 (5-methoxy-1-phenyl-1H-benzo[g]indazol-3(2H)-one)

1-Bromo-4-methoxy-N'-phenyl-2-naphthohydrazide (3.4 mmol), CuI (5 mol %), 1,10-phenanthroline (10 mol %) and Cs$_2$CO$_3$ (4.1 mmol) were put into a round bottom flask, and stirred with slow addition of anhydrous DMSO (34 mL). After then, the reaction mixture was stirred at room temperature for 6 hours. The reaction was quenched by addition of 3M HCl (100 mL), water was added to the reaction mixture, and precipitate was filtered. Filter cake was dried and recrystallized from methanol.

Brownish yellow solid, Yield: 80%.

$^1$H NMR (300 MHz, DMSO-d$_6$) δ: 10.77 (br s, 1H), 8.25 (d, J=8.3 Hz, 1H), 7.60-7.47 (m, 7H), 7.41-7.36 (m, 1H), 7.05 (s, 1H), 4.00 (s, 3H).

Preparation Example 3: Synthesis of Intermediate 3 (2-isopropyl-5-methoxy-1H-benzo[g]indazol-3(2H)-one)

(1) Synthesis of tert-butyl 2-(1-bromo-4-methoxy-2-naphthoyl)-2-isopropylhydrazinecarboxylate Using 1-bromo-4-methoxy-2-naphthoic acid (3.6 mmol, Intermediate 1) and tert-butyl 3-(isopropyl)carbazate (3.9 mmol) as a starting material and a reactant, the title compound was synthesized according to the procedure described in (1) of Preparation Example 3.

White solid, Yield: 86%.

$^1$H NMR (300 MHz, DMSO-d$_6$) δ: 9.40 (br s, 1H), 8.20-8.14 (m, 2H), 7.75-7.59 (m, 2H), 6.83 (br s, 1H), 4.72 (m, 1H), 4.01 (s, 3H), 1.18 (s, 9H), 1.13 (d, J=6.8 Hz, 6H).

(2) Synthesis of tert-butyl 2-isopropyl-5-methoxy-3-oxo-2,3-dihydro-1H-benzo[g]indazole-1-carboxylate Using tert-butyl 2-(1-bromo-4-methoxy-2-naphthoyl)-2-isopropylhydrazinecarboxylate (3.4 mmol) as a starting material, the title compound was synthesized according to the procedure described in (2) of Preparation Example 2.

Brownish solid, Yield: 95%.

$^1$H NMR (300 MHz, DMSO-d$_6$) δ: 8.43-8.33 (m, 2H), 7.66-7.60 (m, 2H), 7.04 (s, 1H), 4.47 (m, 1H), 4.06 (s, 3H), 1.58-1.55 (m, 15H).

(3) Synthesis of Intermediate 3 (2-isopropyl-5-methoxy-1H-benzo[g]indazol-3(2H)-one)

tert-Butyl 2-isopropyl-5-methoxy-3-oxo-2,3-dihydro-1H-benzo[g]indazole-1-carboxylate (2.1 mmol) was put into a round bottom flask and dissolved in anhydrous dichloromethane. Trifluoroacetic acid (42.8 mmol) was carefully added and the reaction mixture was then reacted at room temperature for 4 hours. The reaction mixture was neutralized with slow addition of sat. aq. NaHCO$_3$ solution, and then water was added. The reaction mixture was transferred to a separatory funnel and then extracted three times with ethyl acetate. Combined organic layer was dried over MgSO$_4$ and concentrated under reduced pressure. The crude product was purified by column chromatography.

Yellowish solid, Yield: 91%.

$^1$H NMR (300 MHz, DMSO-d$_6$) δ: 10.36 (br s, 1H), 8.20-8.18 (m, 2H), 7.67-7.65 (m, 2H), 6.91 (br s, 1H), 4.66-4.64 (m, 1H), 3.95 (s, 3H), 1.35 (d, J=7.0 Hz, 6H).

Preparation Example 4: Synthesis of Intermediate 4 (1-isopropyl-2-phenylhydrazine hydrochloride)

(1) Synthesis of tert-butyl 2-isopropyl-1-phenylhydrazinecarboxylate tert-Butyl 3-(isopropyl)carbazate (10 mmol), CuI (5 mol %), 1,10-phenanthroline (10 mol %) and Cs$_2$CO$_3$ (12 mmol) were put into a round bottom flask and dissolved with slow addition of anhydrous DMF (15 mL). Iodobenzene (12 mmol) was added, and the reaction mixture was then stirred at 80° C. for 12 hours. The reaction was quenched with addition of water, and the reaction mixture was transferred to a separatory funnel and then extracted three times with ethyl acetate. Combined organic layer was dried over MgSO$_4$ and concentrated under reduced pressure. The crude product was purified by column chromatography.

Yellowish white solid, Yield: 46%.
$^1$H NMR (300 MHz, CDCl$_3$) δ: 7.48 (d, J=7.9 Hz, 1H), 7.30-7.25 (m, 2H), 7.10-7.05 (m, 1H), 4.64 (br s, 1H), 3.24-3.22 (m, 1H), 1.49 (s, 9H), 0.98 (d, J=6.4 Hz, 6H).

(2) Synthesis of Intermediate 4 (1-Isopropyl-2-phenylhydrazine hydrochloride)

tert-Butyl 2-isopropyl-1-phenylhydrazinecarboxylate (1.998 mmol) was put into a round bottom flask and dissolved in anhydrous dichloromethane (30 mL). Trifluoroacetic acid (39.94 mmol) was added at room temperature, and the reaction mixture was reacted with stirring for 12 hours. The reaction mixture was neutralized with slow addition of sat. aq. NaHCO$_3$ solution, transferred to a separatory funnel and then extracted three times with dichloromethane. Combined organic layer was washed with brine. To the resulting yellow solution, 4M HCl in 1,4-dioxane (12 mmol) was slowly added by syringe and stirred for 30 minutes, and then concentrated under reduced pressure. The crude product was recrystallized from ethyl acetate.

White solid, Yield: 88%.
$^1$H NMR (300 MHz, DMSO-d$_6$) δ: 10.94 (br s, 1H), 8.23 (br s, 1H), 7.34-7.29 (m, 2H), 7.16-7.14 (m, 2H), 7.01-6.96 (m, 1H), 3.55-3.53 (m, 1H), 1.31 (d, J=6.4 Hz, 6H).

Preparation Example 5: Synthesis of Intermediate 5 (5-methoxy-3-phenyl-2,3-dihydro-1H-benzo[e]indazol-1-one)

(1) Synthesis of tert-butyl (1-bromo-4-methoxynaphthalene-2-yl)carbamate

1-Bromo-4-methoxy-2-naphthoic acid (11.59 mmol, Intermediate 1) was put into a round bottom flask and suspended in anhydrous toluene (30 mL). To the reaction mixture, trimethylamine (12.75 mmol) was added and stirred for 5 minutes. After then, diphenyl phosphoryl azide (13.45 mmol) was added, followed by t-BuOH (30.13 mmol) was added. The reaction mixture was stirred at 85° C. for 3 hours. The reaction was quenched by addition of water, and the reaction mixture was transferred to a separatory funnel and then extracted three times with ethyl acetate. Combined organic layer was dried over MgSO$_4$ and concentrated under reduced pressure. The crude product was purified by column chromatography.

White solid, Yield: 98%.
$^1$H NMR (300 MHz, DMSO-d$_6$) δ: 8.64 (s, 1H), 8.15-8.07 (m, 2H), 7.65 (t, J=7.2 Hz, 1H), 7.51 (t, J=7.4 Hz, 1H), 7.28 (s, 1H), 3.96 (s, 3H), 1.48 (s, 9H).

(2) Synthesis of ethyl 2-(tert-butoxycarbonylamino)-4-methoxy-1-naphthoate tert-Butyl (1-bromo-4-methoxynaphthalen-2-yl)carbamate (11.33 mmol) was put into a round bottom flask and dissolved in anhydrous diethyl ether (90 mL). After the reaction mixture was cooled to −20° C., 2.5M n-butyl lithium solution was slowly added dropwise by syringe. After stirring for 2 hours, ethyl chloroformate (11.33 mmol) was slowly added dropwise by syringe, and the reaction mixture was stirred for additional 2 hours. The reaction was quenched with slow addition of sat. NH$_4$Cl solution, and water was poured into the reaction mixture. The reaction mixture was transferred to a separatory funnel and extracted three times with ethyl acetate. Combined organic layer was washed with brine and dried over MgSO$_4$. After concentrated under reduced pressure, the crude product was purified by column chromatography.

Yellowish oil, Yield: 88%.
$^1$H NMR (300 MHz, CDCl$_3$) δ: 9.91 (s, 1H), 8.39 (d, J=8.6 Hz, 1H), 8.20 (d, J=8.1 Hz, 1H), 8.09 (s, 1H), 7.52-7.35 (m, 2H), 4.52 (q, J=7.1 Hz, 2H), 4.08 (s, 2H), 1.55 (s, 9H), 1.49 (t, J=7.1 Hz, 3H).

(3) Synthesis of Ethyl 2-amino-4-methoxy-1-naphthoate

Ethyl 2-(tert-butoxycarbonylamino)-4-methoxy-1-naphthoate (9.93 mmol) was put into a round bottom flask and dissolved in anhydrous dichloromethane (150 mL). Trifluoroacetic acid (198.5 mmol) was added, and the reaction mixture was stirred at room temperature for 4 hours. The reaction mixture was neutralized with sat. aq. NaHCO$_3$ solution and water was added. The reaction mixture was transferred to a separatory funnel and extracted three times with dichloromethane. Combined organic layer was dried over MgSO$_4$ and concentrated under reduced pressure. The crude product was purified by column chromatography.

Light-orange solid, Yield: 95%.
$^1$H NMR (300 MHz, CDCl$_3$) δ: 8.57 (d, J=8.8 Hz, 1H), 8.09 (d, J=8.2 Hz, 1H), 7.48-7.43 (m, 1H), 7.24-7.19 (m, 1H), 6.12 (s, 1H), 6.04 (br s, 2H), 4.45 (q, J=7.1 Hz, 2H), 3.97 (s, 3H), 1.45 (t, J=7.1 Hz, 3H).

(4) Synthesis of Ethyl 2-bromo-4-methoxy-1-naphthoate

Ethyl 2-amino-4-methoxy-1-naphthoate (1.02 mmol) was put into a round bottom flask and dissolved in acetic acid (6 mL). 48% Hydrobromic acid (4 mL) was added, and the reaction mixture was moved into an ice bath to lower the temperature to 0° C., to which sodium nitrite (1.02 mmol) in 2 mL of H$_2$O was slowly added dropwise over 5 minutes by syringe, and then stirred for 2 hours. After 2 hours, CuBr (1.02 mmol) in 5 mL of 48% Hydrobromic acid solution was slowly added by pipette, and stirred for additional 2 hours while slowly raising the temperature to room temperature. The reaction was quenched with addition of water, and the reaction mixture was transferred to a separatory funnel and extracted three times with ethyl acetate. Combined organic layer was dried over MgSO₄ and concentrated under reduced pressure. The crude product was purified by column chromatography.

Colorless oil, Yield: 81%.

$^1$H NMR (300 MHz, CDCl$_3$) δ: 8.24-8.21 (m, 1H), 7.75-7.72 (m, 1H), 7.57-7.50 (m, 2H), 6.93 (s, 1H), 4.53 (q, J=7.1 Hz, 2H), 4.01 (s, 3H), 1.46 (t, J=7.1 Hz, 3H).

(5) Synthesis of 2-Bromo-4-methoxy-1-naphthoic acid

Ethyl 2-bromo-4-methoxy-1-naphthoate (1.57 mmol) and LiOH (25.38 mmol) were put into a round bottom flask and dissolved in THF, methanol and water (1:1:1 v/v). After raising the temperature to 100° C., the reaction mixture was stirred under reflux for 96 hours. The reaction mixture was transferred to a separatory funnel and acidified with 3M HCl to pH 1-2. The mixture was extracted three times with ethyl acetate, and combined organic layer was washed with water and brine in order, and dried over MgSO₄. After concentrated under reduced pressure, the crude product was recrystallized with ethyl acetate and n-hexane.

Pale-Yellowish white solid, Yield: 72.5%.

$^1$H NMR (300 MHz, DMSO-d$_6$) δ: 13.65 (br s, 1H), 8.18-8.15 (m, 1H), 7.75-7.72 (m, 1H), 7.68-7.56 (m, 2H), 7.15 (s, 1H), 4.02 (s, 3H).

(6) Synthesis of 2-Bromo-4-methoxy-N'-phenyl-1-naphthohydrazide

2-Bromo-4-methoxy-1-naphthoic acid (3.60 mmol) was put into a round bottom flask and dissolved in catalytic amount of DMF and anhydrous dichloromethane (20 mL). After slowly adding oxalyl chloride (7.21 mmol) dropwise by syringe, reacted with stirring at room temperature for 2 hours. After 2 hours, residual oxalyl chloride and dichloromethane were removed under reduced pressure. After drying the reaction mixture in vacuo for 30 minutes, residue was dissolved in anhydrous dichloromethane (40 mL), and then phenyl hydrazine (4.33 mmol) and pyridine were slowly added by syringe. The reaction mixture was stirred at room temperature for 2 hours. The reaction was quenched with 1M HCl, and the reaction mixture was transferred to a separatory funnel and then extracted three times with dichloromethane. Combined organic layer was washed with brine and dried over MgSO₄. After concentrated under reduced pressure, the crude product was purified by column chromatography.

Orange solid, Yield: 39%.

$^1$H NMR (300 MHz, DMSO-d$_6$) δ: 10.28 (br s, 1H), 8.16 (d, J=8.2 Hz, 1H), 8.10 (br s, 1H), 7.77 (d, J=8.0 Hz, 1H), 7.64-7.58 (m, 2H), 7.21-7.15 (m, 3H), 6.94 (d, J=8.3 Hz, 2H), 6.75-6.72 (m, 1H), 4.00 (s, 3H).

(7) Synthesis of Intermediate 5 (5-methoxy-3-phenyl-2,3-dihydro-1H-benzo[e]indazol-1-one)

Using the previously prepared 2-bromo-4-methoxy-N'-phenyl-1-naphthohydrazide (1.42 mmol) as a starting material, the title compound was synthesized according to the procedure described in (2) of Preparation Example 2.

Yellow solid, Yield: 97%.

$^1$H NMR (300 MHz, DMSO-d$_6$) δ: 11.39 (br s, 1H), 8.43 (d, J=7.9 Hz, 1H), 8.16 (d, J=7.9 Hz, 1H), 7.76-7.73 (m, 2H), 7.69-7.63 (m, 1H), 7.59-7.53 (m, 2H), 7.48-7.43 (m, 1H), 7.35-7.31 (m, 1H), 7.10 (s, 1H), 4.03 (s, 3H).

Preparation Example 6: Synthesis of Intermediate 6 (tert-butyl 1-isopropylhydrazinecarboxylate)

(1) Synthesis of benzyl 2-isopropylhydrazinecarboxylate

Benzyl carbazate (6.1 mmol) was put into a round bottom flask and dissolved in acetone (18 mmol) and diethyl ether (5 mL). The reaction mixture was stirred for 48 hours. Concentration was conducted under reduced pressure to obtain white solid, to which NaBH$_3$CN (18 mmol) was added, followed by methanol (20 mL) and acetic acid (10 mL) were added, and then stirred at room temperature for 12 hours. After completion of the reaction, methanol was removed under reduced pressure, and residue was dissolved in ethyl acetate, washed with 10% aq. NaHCO$_3$ solution and brine, and dried over MgSO₄. After filtering under reduced pressure, filtrate was concentrated under reduced pressure, and resulting product was used for the next step without further purification.

White solid, Yield: 99%.

$^1$H NMR (300 MHz, CDCl$_3$) δ: 7.45-7.32 (m, 5H), 6.26 (br s, 1H), 5.14 (s, 2H), 3.97 (br s, 1H), 3.19-3.15 (m, 1H), 1.05-1.03 (d, J=6.2 Hz, 6H).

(2) Synthesis of 2-benzyl 1-tert-butyl 1-isopropylhydrazine-1,2-dicarboxylate

Benzyl 2-isopropylhydrazinecarboxylate (6.7 mmol) and 4-dimethylaminopyridine (5 mol %) were put into a round bottom flask and dissolved in acetonitrile (30 mL). To the reaction mixture was slowly added di-tert-butyl dicarbonate (Boc$_2$O, 7.3 mmol) dropwise by syringe, and stirred at room temperature for 48 hours. The reaction mixture was concentrated under reduced pressure. The crude product was purified by column chromatography to give a yellowish oil mixture and used for the next step without further purification.

(3) Synthesis of Intermediate 6 (tert-butyl 1-isopropylhydrazinecarboxylate

2-Benzyl 1-tert-butyl 1-isopropylhydrazine-1,2-dicarboxylate (5.3 mmol) and 10 w % Pd on carbon were put into a round bottom flask and dissolved in methanol (100 mL). The reaction mixture was replaced under reduced pressure with hydrogen gas 5 times, and stirred for 12 hours under a hydrogen balloon. The reaction mixture was filtered through Celite pad and filtrate was concentrated under reduced pressure. The crude product was purified by column chromatography.

Colorless oil, Yield: 48%.

$^1$H NMR (300 MHz, CDCl$_3$) δ: 4.27-4.18 (m, 1H), 3.60 (br s, 2H), 1.48 (s, 9H), 1.12-1.10 (d, J=6.6 Hz, 6H).

Preparation Example 7: Synthesis of Intermediate 7 (1-isopropyl-5-methoxy-1H-benzo[g]indazol-3(2H)-one)

(1) Synthesis of tert-butyl 2-(1-bromo-4-methoxy-2-naphthoyl)-1-isopropylhydrazinecarboxylate Using 1-bromo-4-methoxy-2-naphthoic acid (2.38 mmol) and tert-butyl 1-isopropylhydrazinecarboxylate (2.5 mmol, Intermediate 6) as a starting material and a reactant, the title compound was synthesized according to the procedure described in (1) of Preparation Example 3.

White solid, Yield: 71%.

¹H NMR (300 MHz, DMSO-d₆) δ: 10.13 (br s, 1H), 8.27-8.22 (m, 2H), 7.78-7.75 (m, 1H), 7.71-7.67 (m, 1H), 6.85 (s, 1H), 4.43-4.36 (m, 1H), 4.01 (s, 3H), 1.49 (s, 9H), 1.20-1.18 (d, J=5.9 ppm, 6H).

(2) Synthesis of 1-bromo-N'-isopropyl-4-methoxy-2-naphthohydrazide tert-Butyl 2-(1-bromo-4-methoxy-2-naphthoyl)-1-isopropylhydrazinecarboxylate (1.56 mmol) was put into a round bottom flask and dissolved in dichloromethane (50 mL). Trifluoroacetic acid (31.14 mmol) was added, and the reaction mixture was stirred at room temperature for 12 hours. When the reaction was completed, the reaction mixture was neutralized with sat. aq. NaHCO₃ solution, transferred to a separatory funnel and then extracted with dichloromethane. Combined organic layer was washed with brine and dried over MgSO₄. After filtering under reduced pressure, filtrate was concentrated under reduced pressure. The resulting product was used for the next step without further purification.

White solid, Yield: 99%.
¹H NMR (300 MHz, DMSO-d₆) δ: 9.88 (br s, 1H), 8.24-8.20 (m, 2H), 7.78-7.73 (m, 1H), 7.68-7.63 (m, 1H), 4.95 (br s, 1H), 4.01 (s, 3H), 3.22-3.17 (m, 1H), 1.09-1.07 (d, J=6.2 ppm, 6H).

(3) Synthesis of Intermediate 7 (1-isopropyl-5-methoxy-1H-benzo[g]indazol-3(2H)-one Using the previously prepared 1-bromo-N'-isopropyl-4-methoxy-2-naphthohydrazide as a starting material, the title compound was synthesized according to the procedure described in (2) of Preparation Example 2.

Yellow solid, Yield: 94%.
¹H NMR (300 MHz, DMSO-d₆) δ: 10.37 (br s, 1H), 8.44-8.40 (m, 1H), 8.30-8.27 (m, 1H), 7.69-7.61 (m, 2H), 6.96 (s, 1H), 5.33-5.25 (m, 1H), 3.96 (s, 3H), 1.48-1.46 (d, J=6.1 Hz, 6H).

Preparation Example 8: Synthesis of Intermediate 8 (5-methoxy-1-(4-(trifluoromethyl)phenyl)-1H-benzo[g]indazol-3(2H)-one)

(1) Synthesis of 1-bromo-4-methoxy-N'-(4-(trifluoromethyl)phenyl)-2-naphthohydrazide Using 1-bromo-4-methoxy-2-naphthoic acid (3.01 mmol, Intermediate 1) and (4-(trifluoromethyl)phenyl)hydrazine (3.3 mmol) as a starting material and a reactant, the title compound was synthesized according to the procedure described in (1) of Preparation Example 3.

Yellowish white solid, Yield: 83%.
¹H NMR (300 MHz, DMSO-d₆) δ: 10.42 (br s, 1H), 8.67 (br s, 1H), 8.29-8.25 (m, 2H), 7.83-7.77 (m, 1H), 7.72-7.67 (m, 1H), 7.56-7.53 (m, 2H), 7.08-7.05 (m, 2H), 7.01 (s, 1H), 4.05 (s, 3H).

(2) Synthesis of Intermediate 8 (5-methoxy-1-(4-(trifluoromethyl)phenyl)-1H-benzo[g]indazol-3(2H)-one)

Using the previously prepared 1-bromo-4-methoxy-N'-(4-(trifluoromethyl)phenyl)-2-naphthohydrazide as a starting material, the title compound was synthesized according to the procedure described in (2) of Preparation Example 2.

Brownish yellow solid, Yield: 70%.
¹H NMR (300 MHz, DMSO-d₆) δ: 11.07 (br s, 1H), 8.31 (d, J=7.9 Hz, 1H), 7.93 (d, J=8.4 Hz, 1H), 7.77 (d, J=8.6 Hz, 1H), 7.65-7.51 (m, 3H), 7.09 (s, 1H), 4.03 (s, 3H).

Preparation Example 9: Synthesis of Intermediate 9 (1-(4-fluorophenyl)-5-methoxy-1H-benzo[g]indazol-3(2H)-one)

(1) Synthesis of 1-bromo-N'-(4-fluorophenyl)-4-methoxy-2-naphthohydrazide

Using 1-bromo-4-methoxy-2-naphthoic acid (2.0 mmol, Intermediate 1) and (4-fluorophenyl)hydrazine hydrochloride (2.2 mmol) as a starting material and a reactant, the title compound was synthesized according to the procedure described in (1) of Preparation Example 3.

Pale-orange solid, Yield: 57%.
¹H NMR (300 MHz, DMSO-d₆) δ: 10.27 (br s, 1H), 8.27-8.23 (m, 2H), 7.97 (br s, 1H), 7.81-7.66 (m, 2H), 7.07-6.93 (m, 5H), 4.05 (s, 3H).

(2) Synthesis of Intermediate 9 (1-(4-fluorophenyl)-5-methoxy-1H-benzo[g]indazol-3(2H)-one)

Using the previously prepared 1-bromo-N'-(4-fluorophenyl)-4-methoxy-2-naphthohydrazide as a starting material, the title compound was synthesized according to the procedure described in (2) of Preparation Example 2.

Yellowish solid, Yield: 69%.
¹H NMR (300 MHz, DMSO-d₆) δ: 10.79 (br s, 1H), 8.29-8.26 (m, 1H), 7.61-7.56 (m, 3H), 7.46-7.40 (m, 4H), 7.07 (s, 1H), 4.01 (s, 3H).

Preparation Example 10: Synthesis of Intermediate 10 (5-methoxy-2-phenyl-1H-benzo[g]indazol-3(2H)-on)

(1) Synthesis of tert-butyl 2-(1-bromo-4-methoxy-2-naphthoyl)-2-phenylhydrazinecarboxylate Using the previously prepared 1-bromo-4-methxy-2-naphthoic acid (8.0 mmol, Intermediate 1) and 1-Boc-2-phenylhydrazine (9.6 mmol) as a starting material and a reactant, the title compound was synthesized according to the procedure described in (5) of Preparation Example 6 and resulting white solid was used for next step without further purification.

(2) Synthesis of tert-butyl 5-methoxy-3-oxo-2-phenyl-2,3-dihydro-1H-benzo[g]indazole-1-carboxylate Using the previously prepared tert-butyl 2-(1-bromo-4-methoxy-2-naphthoyl)-2-phenylhydrazinecarboxylate as a starting material, the title compound was synthesized according to the procedure described in (5) of Preparation Example 6.

Brown solid, Yield: 98%.
¹H NMR (300 MHz, CDCl₃) δ: 8.67-8.63 (m, 1H), 8.42-8.39 (m, 1H), 7.71-7.67 (m, 4H), 7.50-7.44 (m, 2H), 7.28-7.23 (m, 1H), 7.14 (s, 1H), 4.08 (s, 3H), 1.23 (s, 9H).

(3) Synthesis of Intermediate 10 (5-methoxy-2-phenyl-1H-benzo[g]indazol-3(2H)-one)

Using the previously prepared tert-butyl 5-methoxy-3-oxo-2-phenyl-2,3-dihydro-1H-benzo[g]indazole-1-carboxylate as a starting material, the title compound was synthesized according to the procedure described in (2) of Preparation Example 7.

Pale-brown solid, Yield: 90%.

$^1$H NMR (300 MHz, DMSO-d$_6$) δ: 11.18 (br s, 1H), 8.29-8.21 (m, 2H), 8.01 (d, J=7.7 Hz, 2H), 7.75-7.71 (m, 2H), 7.57-7.52 (m, 2H), 7.30-7.25 (m, 1H), 7.03 (s, 1H), 4.02 (s, 3H).

Preparation Example 11: Synthesis of Intermediate 11 (1-bromo-6-fluoro-4-methoxy-2-naphthoic acid)

(1) Synthesis of methyl 6-fluoro-4-hydroxy-2-naphthoate

Using 4-fluorobenzaldehyde (16.3 mmol) as a starting material, the title compound was synthesized according to the procedure described in (1) of Preparation Example 1.

White solid, Yield: overall 26%.

$^1$H NMR (300 MHz, CDCl$_3$) δ: 8.18 (s, 1H), 7.91-7.79 (m, 1H), 7.42 (s, 1H), 7.33-7.27 (m, 1H), 5.68 (br s, 1H), 3.94 (s, 3H).

(2) Synthesis of methyl 6-fluoro-4-methoxy-2-naphthoate

Using the previously prepared methyl 6-fluoro-1-hydroxy-3-naphthoate as a starting material, the title compound was synthesized according to the procedure described in (2) of Preparation Example 1 and resulting compound was used for next step without further purification.

(3) Synthesis of methyl 1-bromo-6-fluoro-4-methoxy-2-naphthoate

Using the previously prepared methyl 6-fluoro-4-methoxy-2-naphthoate as a starting material, the title compound was synthesized according to the procedure described in (3) of Preparation Example 1.

Pale-orange solid, Yield: 92%.

$^1$H NMR (300 MHz, CDCl$_3$) δ: 8.46-8.41 (m, 1H), 7.92-7.87 (m, 1H), 7.44-7.39 (m, 1H), 7.06 (s, 1H), 4.03 (s, 3H), 4.01 (s, 3H).

(4) Synthesis of Intermediate 11 (1-bromo-6-fluoro-4-methoxy-2-naphthoic acid)

Using the previously prepared methyl 1-bromo-6-fluoro-4-methoxy-2-naphthoate as a starting material, the title compound was synthesized according to the procedure described in (4) of Preparation Example 1.

White sold, Yield: 96%.

$^1$H NMR (300 MHz, CDCl$_3$) δ: 8.54-8.49 (m, 1H), 7.94-7.91 (m, 1H), 7.47-7.41 (m, 1H), 7.25 (s, 1H), 4.06 (s, 3H).

Preparation Example 12: Synthesis of Intermediate 12 (7-fluoro-5-methoxy-1-phenyl-1H-benzo[g]indazol-3(2H)-one)

(1) Synthesis of 1-bromo-6-fluoro-4-methoxy-N'-phenyl-2-naphthohydrazide

Using 1-bromo-6-fluoro-4-methoxy-2-naphthoic acid (3.34 mmol, Intermediate 11) as a starting material, the title compound was synthesized according to the procedure described in (6) of Preparation Example 5.

Pinkish solid, Yield: 90%.

$^1$H NMR (300 MHz, DMSO-d$_6$) δ: 10.25 (s, 1H), 8.36-8.31 (m, 1H), 7.93-7.88 (m, 1H), 7.79-7.68 (m, 1H), 7.23-7.17 (m, 2H), 7.03 (s, 1H), 6.96-6.93 (m, 2H), 6.80-6.73 (m, 1H), 4.06 (s, 3H).

(2) Synthesis of Intermediate 12 (7-fluoro-5-methoxy-1-phenyl-1H-benzo[g]indazol-3(2H)-one)

Using the previously prepared 1-bromo-6-fluoro-4-methoxy-N'-phenyl-2-naphthohydrazide (3.3 mmol) as a starting material, the title compound was synthesized according to the procedure described in (2) of Preparation Example 2.

Grey solid, Yield: 77%.

$^1$H NMR (300 MHz, DMSO-d$_6$) δ: 10.85 (br s, 1H), 7.93-7.88 (m, 1H), 7.71-7.52 (m, 6H), 7.40-7.33 (m, 1H), 7.15 (s, 1H), 4.03 (s, 3H).

Preparation Example 13: Synthesis of Intermediate 13 (1-bromo-4-methoxy-6-nitro-2-naphthoic acid)

(1) Synthesis of methyl 4-hydroxy-6-nitro-2-naphthoate

Using 4-nitrobenzaldehyde (150 mmol) as a starting material, the title compound was synthesized according to the procedure described in (1) of Preparation Example 1.

Yellow solid, Yield: overall 8%.

$^1$H NMR (300 MHz, DMSO-d$_6$) δ: 11.29 (br s, 1H), 9.00 (s, 1H), 8.32-8.24 (m, 1H), 8.21 (s, 1H), 7.50 (s, 1H), 3.92 (s, 3H).

(2) Synthesis of methyl 4-methoxy-6-nitro-2-naphthoate

Using the previously prepared methyl 4-hydroxy-6-nitro-2-naphthoate as a starting material, the title compound was synthesized according to the procedure described in (2) of Preparation Example 1, as a yellow solid, which was used the next step without further purification.

(3) Synthesis of methyl 1-bromo-4-methoxy-6-nitro-2-naphthoate

Using the previously prepared methyl 4-methoxy-6-nitro-2-naphthoate as a starting material, the title compound was synthesized according to the procedure described in (3) of Preparation Example 1.

Yellow solid, Yield: 62%.

$^1$H NMR (300 MHz, CDCl$_3$) δ: 8.24-8.23 (m, 1H), 8.56-8.53 (m, 1H), 8.41-8.37 (m, 1H), 7.12 (s, 1H), 4.09 (s, 3H), 4.04 (s, 3H).

(4) Synthesis of Intermediate 13 (1-bromo-4-methoxy-6-nitro-2-naphthoic acid)

Using the previously prepared methyl 1-bromo-4-methoxy-6-nitro-2-naphthoate as a starting material, the title compound was synthesized according to the procedure described in (4) of Preparation Example 1.

Yellow solid, Yield: 95%.

$^1$H NMR (300 MHz, DMSO-d$_6$) δ: 9.02 (s, 1H), 8.50-8.35 (m, 2H), 7.33 (s, 1H), 4.10 (s, 3H).

Preparation Example 14: Synthesis of Intermediate 14 (5-methoxy-7-nitro-1-phenyl-1H-benzo[g]inda-zol-3(2H)-one)

(1) Synthesis of 1-bromo-4-methoxy-6-nitro-N'-phenyl-2-naphthohydrazide

Using 1-bromo-4-methoxy-6-nitro-2-naphthoic acid (4.14 mmol, Intermediate 13) as a starting material, the title compound was synthesized according to the procedure described in (6) of Preparation Example 5.

Yellowish white solid, Yield: 80%.

$^1$H NMR (300 MHz, DMSO-$d_6$) δ: 10.36 (br s, 1H), 9.09 (s, 1H), 8.50 (s, 1H), 7.29-7.18 (m, 4H), 7.01-6.84 (m, 3H), 4.15 (s, 3H).

(2) Synthesis of Intermediate 14 (5-methoxy-7-nitro-1-phenyl-1H-benzo[g]indazol-3(2H)-one)

Using the previously prepared 1-bromo-4-methoxy-6-nitro-N'-phenyl-2-naphthohydrazide (3.4 mmol) as a starting material, the title compound was synthesized according to the procedure described in (2) of Preparation Example 2.

Yellow solid, Yield: 74%.

$^1$H NMR (300 MHz, DMSO-$d_6$) δ: 11.09 (br s, 1H), 9.08 (s, 1H), 8.23-8.19 (m, 1H), 7.71-7.56 (m, 6H), 7.29 (s, 1H), 4.09 (s, 3H).

Preparation Example 15: Synthesis of Intermediate 15 (1,6-dibromo-4-methoxy-2-naphthoic acid)

(1) Synthesis of ethyl 6-bromo-4-hydroxy-2-naphthoate

Using 4-bromobenzaldehyde (150 mmol) and diethyl succinate (165 mmol) as a starting material and a reactant, the title compound was synthesized according to the procedure described in (1) of Preparation Example 1.

Pale-brown solid, Yield: overall 10%.

$^1$H NMR (300 MHz, CDCl$_3$) δ: 8.42 (s, 1H), 8.18 (s, 1H), 7.80-7.77 (m, 1H), 7.65-7.62 (m, 1H), 7.50 (s, 1H), 5.74 (br s, 1H), 4.44 (q, J=6.0 Hz, 2H), 1.45 (t, J=6.0 Hz, 3H).

(2) Synthesis of ethyl 6-bromo-4-methoxy-2-naphthoate

Using the previously prepared ethyl 6-bromo-4-hydroxy-2-naphthoate as a starting material, the title compound was synthesized according to the procedure described in (2) of Preparation Example 1 and used for next step without further purification.

(3) Synthesis of ethyl 1,6-dibromo-4-methoxy-2-naphthoate

Using the previously prepared ethyl 6-bromo-4-methoxy-2-naphthoate as a starting material, the title compound was synthesized according to the procedure described in (3) of Preparation Example 1.

Orange solid, Yield: 60%.

$^1$H NMR (300 MHz, CDCl$_3$) δ: 8.45 (s, 1H), 8.26 (d, J=9.2 Hz, 1H), 7.73-7.70 (m, 1H), 7.02 (s, 1H), 4.48 (q, J=7.2 Hz, 2H), 4.03 (s, 3H), 1.46 (t, J=7.2 Hz, 3H).

(4) Synthesis of Intermediate 15 (1,6-dibromo-4-methoxy-2-naphthoic acid)

Using the previously prepared ethyl-1,6-dibromo-4-methoxy-2-naphthoate as a starting material, the title compound was synthesized according to the procedure described in (4) of Preparation Example 1.

White solid, Yield: 90%.

$^1$H NMR (300 MHz, DMSO-$d_6$) δ: 8.36 (s, 1H), 8.23-8.20 (m, 1H), 7.79-7.89 (m, 1H), 7.21 (s, 1H), 4.03 (s, 3H).

Preparation Example 16: Synthesis of Intermediate 16 (7-bromo-5-methoxy-1-phenyl-1H-benzo[g]indazol-3(2H)-one)

(1) Synthesis of 1,6-dibromo-4-methoxy-N'-phenyl-2-naphthohydrazide

Using 1,6-dibromo-4-methoxy-2-naphthoic acid (1.39 mmol, Intermediate 15) as a starting material, the title compound was synthesized according to the procedure described in (6) of Preparation Example 5.

Orange solid, Yield: 92%.

$^1$H NMR (300 MHz, DMSO-$d_6$) δ: 10.29 (br s, 1H), 8.39-8.38 (m, 1H), 8.21-8.18 (m, 1H), 7.95-7.91 (m, 1H), 7.23-7.18 (m, 2H), 7.05 (s, 1H), 6.96-6.93 (m, 2H), 6.80-6.73 (m, 1H), 4.06 (s, 3H).

(2) Synthesis of Intermediate 16 (7-bromo-5-methoxy-1-phenyl-1H-benzo[g]indazol-3(2H)-one)

Using the previously prepared 1,6-dibromo-4-methoxy-N'-phenyl-2-naphthohydrazide (1.1 mmol) as a starting material, the title compound was synthesized according to the procedure described in (2) of Preparation Example 2.

Pale-brown solid, Yield: 60%.

$^1$H NMR (300 MHz, DMSO-$d_6$) δ: 10.93 (br s, 1H), 8.38-8.37 (m, 1H), 7.62-7.50 (m, 6H), 7.45-7.42 (m, 1H), 7.15 (s, 1H), 4.02 (s, 3H).

Preparation Example 17: Synthesis of Intermediate 17 (4-(benzyloxy)-1-bromo-2-naphthoic acid)

(1) Synthesis of methyl 4-(benzyloxy)-2-naphthoate

Methyl 1-hydroxy-3-naphthoate (0.5 mmol) was dissolved in DMF (3 mL), and K$_2$CO$_3$ (1.0 mmol) and benzyl bromide (0.75 mmol) were added at room temperature. After stirring for 2 hours, the reaction was quenched by adding water. The resulting mixture was extracted with ethyl acetate, and separated organic layer was washed with brine and dried over MgSO$_4$. Obtained crude product was used for the next step without further purification.

(2) Synthesis of methyl 4-(benzyloxy)-1-bromo-2-naphthoate

Methyl 4-(benzyloxy)-2-naphthoate (0.46 mmol) was dissolved in acetonitrile (5 mL). N-Bromosuccinimide (0.45 mmol) was then added in one-portion, and the reaction mixture was stirred at room temperature for 3 days. When the reaction was completed, solvent was removed under reduced pressure, and purification was conducted by column chromatography.

White solid, Yield: 91%.

¹H NMR (300 MHz, CDCl₃) δ: 8.43-8.34 (m, 2H), 7.70-7.38 (m, 7H), 7.15 (s, 1H), 5.26 (s, 2H), 4.01 (s, 3H).

(3) Synthesis of Intermediate 17 (4-(benzyloxy)-1-bromo-2-naphthoic acid)

Methyl 4-(benzyloxy)-1-bromo-2-naphthoate (1.47 mmol) was dissolved in a mixture of THF (10 mL), methanol (10 mL) and water (10 mL). NaOH (7 mmol) was then added, and the reaction mixture was stirred at room temperature for 1 day. When the reaction was completed, organic solvent was removed under reduced pressure, and water was added and then conc. HCl was added so as to lower pH. Aqueous layer was extracted with ethyl acetate and dried over MgSO₄. Obtained compound was recrystallized with dichloromethane.

White solid, Yield: 95%.
¹H NMR (300 MHz, DMSO-d₆) δ: 13.64 (br s, 1H), 8.29 (d, J=8.4 Hz, 2H), 7.81-7.67 (m, 2H), 7.59-7.56 (m, 2H), 7.47-7.35 (m, 3H), 7.28 (s, 1H), 5.37 (s, 2H).

Preparation Example 18: Synthesis of Intermediate 18 (5-(benzyloxy)-1-phenyl-1,2-dihydro-3H-benzo[g]indazol-3-one)

(1) Synthesis of 4-(benzyloxy)-1-bromo-N'-phenyl-2-naphthohydrazide 4-(Benzyloxy)-1-bromo-2-naphthoic acid (1.5 mmol, Intermediate 17) was dissolved in dichloromethane (30 mL) and 5 drops of DMF was added. Oxalyl chloride (2.9 mmol) was added at room temperature under argon atmosphere, and reacted for 2 hours. After the reaction was completed, the solvent was removed under reduced pressure, the resulting acid chloride intermediate was dissolved in dichloromethane (20 mL), to which a mixture of phenyl hydrazine (1.7 mmol), pyridine (2.9 mmol) and dichloromethane (20 mL) was added. After reacting at room temperature for 10 hours, the reaction was quenched by adding water. Aqueous layer was extracted with dichloromethane, and organic layer was dried over MgSO₄. Resulting compound was recrystallized with ethyl acetate and hexane.

Yellow solid, Yield: 85%.
¹H NMR (300 MHz, DMSO-d₆) δ: 10.22 (br s, 1H), 8.31 (d, J=8.4 Hz, 1H), 8.25 (d, J=8.4 Hz, 1H), 7.99 (br s, 1H), 7.81-7.66 (m, 2H), 7.59-7.56 (m, 2H), 7.47-7.37 (m, 3H), 7.22-7.17 (m, 2H), 7.09 (s, 1H), 6.93-6.91 (m, 2H), 6.77-6.72 (m, 1H), 5.40 (s, 2H).

(2) Synthesis of Intermediate 18 (5-(benzyloxy)-1-phenyl-1,2-dihydro-3H-benzo[g]indazol-3-one)

4-(Benzyloxy)-1-bromo-N'-phenyl-2-naphthohydrazide (1.2 mmol), CuI (0.12 mmol), L-proline (0.24 mmol) and K₂CO₃ (2.4 mmol) were put into a round bottom flask and dissolved in DMSO (10 mL). The reaction mixture was stirred at room temperature for 12 hours, and the reaction was quenched by adding water. The resulting mixture was neutralized with conc. HCl and extracted with ethyl acetate. Organic layer was dried over MgSO₄. The crude product was purified by column chromatography.

Grey solid, Yield: 58%.
¹H NMR (300 MHz, DMSO-d₆) δ: 10.83 (br s, 1H), 8.33 (d, J=8.3 Hz, 1H), 7.61-7.35 (m, 13H), 7.17 (s, 1H), 5.33 (s, 2H).

Example 1: Synthesis of Compound 1 (1-phenyl-1H-benzo[g]indazol-3,4,5(2H)-trione)

(1) Synthesis of 5-hydroxy-1-phenyl-1H-benzo[g]indazol-3(2H)-one

5-Methoxy-1-phenyl-1H-benzo[g]indazol-3(2H)-one (0.75 mmol, Intermediate 2) was put into a round bottom flask and suspended in dichloromethane (7.5 mL), to which 1M BBr₃ in CH₂Cl₂ (1.88 mmol) was slowly added. After reacting for 3 hours, water was slowly added to quench the reaction. The reaction mixture was transferred to a separatory funnel and then extracted three times with ethyl acetate. Combined organic layer was washed with brine and dried over MgSO₄. After concentrated under reduced pressure, the crude product was purified by column chromatography.

Brownish yellow solid, Yield: 92%.
¹H NMR (300 MHz, DMSO-d₆) δ: 10.67 (br s, 1H), 9.89 (br s, 1H), 8.24 (d, J=8.3 Hz, 1H), 7.59-7.46 (m, 7H), 7.38-7.32 (m, 1H), 6.97 (s, 1H).

(2) Synthesis of Compound 1 (1-phenyl-1H-benzo[g]indazol-3,4,5(2H)-trione)

5-Hydroxy-1-phenyl-1H-benzo[g]indazol-3(2H)-one (0.38 mmol) was put into a round bottom flask and dissolved in DMF (10 mL). IBX (0.38 mmol) was added in one-portion, and the reaction mixture was stirred for 2 hours. When the reaction was completed, the reaction was quenched with sat. aq. NaHCO₃. The reaction mixture was transferred to a separatory funnel and then extracted three times with ethyl acetate. Combined organic layer was dried over MgSO₄. After concentrated under reduced pressure, the crude product was purified by column chromatography.

Orange solid, Yield: 96%.
¹H NMR (300 MHz, DMSO-d₆) δ: 7.99 (d, J=7.3 Hz, 1H), 7.67-7.62 (m, 5H), 7.52-7.42 (m, 2H), 6.72 (d, J=7.32 Hz, 1H).

Example 2: Synthesis of Compound 2 (3-isopropoxy-1-phenyl-1H-benzo[g]indazol-4,5-dione)

1-Phenyl-1H-benzo[g]indazol-3,4,5(2H)-trione (0.27 mmol, Compound 1) and K₂CO₃ (0.80 mmol) were put into a round bottom flask and dissolved in anhydrous DMSO (3 mL). 2-Bromopropane (0.48 mmol) was added, and the reaction mixture was stirred at 75° C. for 2 hours. After confirming the completion of the reaction with TLC, the reaction was quenched by adding water. The reaction mixture was transferred to a separatory funnel and then extracted three times with ethyl acetate. Combined organic layer was dried over MgSO₄. After concentrated under reduced pressure, the crude product was purified by column chromatography.

white solid, Yield: 75%.
¹H NMR (300 MHz, DMSO-d₆) δ: 8.00 (d, J=7.7 Hz, 1H), 7.68-7.61 (m, 5H), 7.53-7.45 (m, 2H), 6.73 (d, J=7.5 Hz, 1H), 4.98 (m, 1H), 1.36 (d, J=6.2 Hz, 6H).

Example 3: Synthesis of Compound 3(2-isopropyl-1-methyl-1H-benzo[g]indazol-3,4,5(2H)-trione)

(1) Synthesis of 2-isopropyl-5-methoxy-1-methyl-1H-benzo[g]indazol-3(2H)-one

2-Isopropyl-5-methoxy-1H-benzo[g]indazol-3(2H)-one (0.90 mmol, Intermediate 3) and K₂CO₃ (1.80 mmol) were put into a round bottom flask and dissolved in anhydrous DMSO (3.0 mL). When reactants were well dissolved, iodomethane (1.80 mmol) was added, and the resulting mixture was stirred at room temperature for 4 hours. The reaction was quenched with addition of water, and the reaction mixture was transferred to a separatory funnel and then extracted three times with ethyl acetate. Combined organic layer was dried over MgSO$_4$. After concentrated under reduced pressure, the crude product was purified by column chromatography.

Pinkish brown solid, Yield: 70%.

$^1$H NMR (300 MHz, CDCl$_3$) δ: 8.40-8.36 (m, 1H), 8.05-8.00 (m, 1H), 7.63-7.60 (m, 2H), 7.06 (s, 1H), 4.54-4.56 (m, 1H), 4.01 (s, 3H), 1.54 (d, J=7.0 Hz, 6H).

(2) Synthesis of 5-hydroxy-2-isopropyl-1-methyl-1H-benzo[g]indazol-3(2H)-one

Using the previously prepared 2-isopropyl-5-methoxy-1-methyl-1H-benzo[g]indazol-3(2H)-one (0.64 mmol) as a starting material, the title compound was synthesized according to the procedure described in (1) of Example 1.

Brownish yellow solid, Yield: 99%.

$^1$H NMR (300 MHz, DMSO-d$_6$) δ: 10.18 (br s, 1H), 8.30-8.27 (m, 1H), 8.14-8.11 (m, 1H), 7.69-7.63 (m, 2H), 6.89 (s, 1H), 4.37-4.39 (m, 1H), 3.29 (s, 3H), 1.44 (d, J=7.0 Hz, 6H).

(3) Synthesis of Compound 3(2-isopropyl-1-methyl-1H-benzo[g]indazol-3,4,5 (2H)-trione)

Using the previously prepared 5-hydroxy-2-isopropyl-1-methyl-1H-benzo[g]indazol-3(2H)-one (0.63 mmol) as a starting material, the title compound was synthesized according to the procedure described in (2) of Example 1.

Orange solid, Yield: 84%

$^1$H NMR (300 MHz, DMSO-d$_6$) δ: 8.07 (d, J=7.7 Hz, 2H), 7.86 (t, J=7.7 Hz, 1H), 7.74 (t, J=7.6 Hz, 1H), 4.56-4.54 (m, 1H), 3.99 (s, 3H), 1.46 (d, J=6.8 Hz, 6H).

Example 4: Synthesis of Compound 4 (2-isopropyl-3-methoxy-2H-benzo[g]indazol-4,5-dione)

(1) Synthesis of 2-isopropyl-3,5-dimethoxy-2H-benzo[g]indazole

Using 2-isopropyl-5-methoxy-1H-benzo[g]indazol-3 (2H)-one (0.90 mmol, Intermediate 3) as a starting material, the title compound was synthesized according to the procedure described in (1) of Example 3.

Brownish yellow solid, Yield: 28%.

$^1$H NMR (300 MHz, CDCl$_3$) δ: 8.51 (d, J=7.5 Hz, 1H), 8.17 (d, J=7.5 Hz, 1H), 7.58-7.49 (m, 2H), 6.70 (s, 1H), 4.78-4.76 (m, 1H), 4.22 (s, 3H), 3.97 (s, 3H), 1.58 (d, J=6.8 Hz, 6H).

(2) Synthesis of 2-isopropyl-3-methoxy-2H-benzo[g]indazol-5-ol

Using the previously prepared 2-isopropyl-3,5-dimethoxy-2H-benzo[g]indazole (0.28 mmol, 2) as a starting material, the title compound was synthesized according to the procedure described in (1) of Example 1.

Brownish yellow solid, Yield: 88%.

$^1$H NMR (300 MHz, DMSO-d$_6$) δ: 9.51 (br s, 1H), 8.31-8.28 (m, 1H), 8.07-8.04 (m, 1H), 7.53-7.49 (m, 2H), 6.81 (s, 1H), 4.71-4.69 (m, 1H), 4.15 (s, 3H), 1.46 (d, J=6.6 Hz, 6H).

(3) Synthesis of Compound 4 (2-isopropyl-3-methoxy-2H-benzo[g]indazol-4,5-dione)

Using the previously prepared 2-isopropyl-3-methoxy-2H-benzo[g]indazol-5-ol (0.25 mmol, 3) as a starting material, the title compound was synthesized according to the procedure described in (2) of Example 1.

Brownish yellow solid, Yield: 65%.

$^1$H NMR (300 MHz, DMSO-d$_6$) δ: 7.97-7.92 (m, 2H), 7.72 (td, J=7.6, 1.35 Hz, 1H), 7.53-7.48 (m, 1H), 4.58-4.56 (m, 1H), 4.36 (s, 3H) 1.40 (d, J=6.8 Hz, 6H).

Example 5: Synthesis of Compound 5 (2-methyl-1-phenyl-1H-benzo[g]indazol-3,4,5(2H)-trione)

(1) 5-methoxy-2-methyl-1-phenyl-1H-benzo[g]indazol-3(2H)-one

Using 5-methoxy-2-methyl-1-phenyl-1H-benzo[g]indazol-3(2H)-one (0.41 mmol, Intermediate 2) as a starting material, the title compound was synthesized according to the procedure described in (1) of Example 3.

Yellow solid, Yield: 26.5%.

$^1$H NMR (300 MHz, DMSO-d$_6$) δ: 8.26 (d, J=8.3 Hz, 1H), 7.61-7.52 (m, 4H), 7.42-7.34 (m, 3H), 7.28-7.25 (m, 1H), 7.11 (s, 1H), 4.04 (s, 3H), 3.16 (s, 3H).

(2) Synthesis of 5-hydroxy-2-methyl-1-phenyl-1H-benzo[g]indazol-3(2H)-one

Using the previously prepared 5-methoxy-2-methyl-1-phenyl-1H-benzo[g]indazol-3(2H)-one as a starting material, the title compound was synthesized according to the procedure described in (1) of Example 1.

Yellow solid, Yield: 73.4%.

$^1$H NMR (300 MHz, DMSO-d$_6$) δ: 10.35 (br s, 1H), 8.25 (d, J=8.4 Hz, 1H), 7.57-7.52 (m, 4H), 7.39-7.33 (m, 3H), 7.26-7.24 (m, 1H), 7.03 (s, 1H), 3.15 (s, 3H).

(3) Synthesis of Compound 5 (2-methyl-1-phenyl-1H-benzo[g]indazol-3,4,5(2H)-trione)

Using the previously prepared 5-hydroxy-2-methyl-1-phenyl-1H-benzo[g]indazol-3(2H)-one as a starting material, the title compound was synthesized according to the procedure described in (2) of Example 1.

Yellow solid, Yield: 96%.

$^1$H NMR (300 MHz, DMSO-d$_6$) δ: 8.04 (d, J=7.5 Hz, 1H), 7.83-7.73 (m, 5H), 7.59 (t, J=7.6 Hz, 1H), 7.44 (t, J=7.8 Hz, 1H), 6.55 (d, J=7.9 Hz, 1H), 3.06 (s, 3H).

Example 6: Synthesis of Compound 6 (3-methoxy-1-phenyl-1H-benzo[g]indazol-4,5-dione)

(1) Synthesis of 3,5-dimethoxy-1-phenyl-1H-benzo[g]indazole

Using Intermediate 2 as a starting material, the title compound was synthesized according to the procedure described in (1) of Example 5.

Yellow solid, Yield: 73.1%.

¹H NMR (300 MHz, CDCl₃) δ: 8.35 (d, J=8.3 Hz), 7.59-7.45 (m, 7H), 7.34-7.25 (m, 1H), 6.93 (s, 1H), 4.16 (s, 3H), 4.04 (s, 3H).

(2) Synthesis of 3-methoxy-1-phenyl-1H-benzo[g]indazol-5-ol

Using the previously prepared 3,5-dimethoxy-1-phenyl-1H-benzo[g]indazole as a starting material, the title compound was synthesized according to the procedure described in (1) of Example 1.
Yellowish white solid, Yield: 72%.
¹H NMR (300 MHz, CDCl₃) δ: 8.30 (d, J=8.4 Hz, 1H), 7.58-7.45 (m, 7H), 7.35-7.30 (m, 1H), 6.96 (s, 1H), 5.17 (br s, 1H), 4.11 (s, 3H).

(3) Synthesis of Compound 6 (3-methoxy-1-phenyl-1H-benzo[g]indazol-4,5-dione)

Using the previously prepared 3-methoxy-1-phenyl-1H-benzo[g]indazol-5-ol as a starting material, the title compound was synthesized according to the procedure described in (2) of Example 1.
Yellow solid, Yield: 92%.
¹H NMR (300 MHz, DMSO-d₆) δ: 8.01 (d, J=7.7 Hz, 1H), 7.69-7.63 (m, 5H), 7.55-7.44 (m, 2H), 6.75 (d, 7.7 Hz, 1H), 3.97 (s, 3H).

Example 7: Synthesis of Compound 7 (2-ethyl-1-phenyl-1H-benzo[g]indazol-3,4,5(2H)-trione)

(1) Synthesis of 5-methoxy-2-ethyl-1-phenyl-1H-benzo[g]indazol-3(2H)-one

Using 5-methoxy-2-methyl-1-phenyl-1H-benzo[g]indazol-3(2H)-one (1.09 mmol, Intermediate 2) and iodoethane (5.43 mmol) as a starting material and a reactant, the title compound was synthesized according to the procedure described in (1) of Example 3.
Yellow solid, Yield: 14.2%.
¹H NMR (300 MHz, DMSO-d₆) δ: 8.33 (d, J=8.4 Hz, 1H), 7.52-7.44 (m, 4H), 7.36-7.26 (m, 4H), 7.18 (s, 1H), 4.05 (s, 3H), 3.75 (q, J=7.1 Hz, 2H), 1.24 (t, J=7.1 Hz, 3H).

(2) Synthesis of 5-hydroxy-2-ethyl-1-phenyl-1H-benzo[g]indazol-3(2H)-one

Using the previously prepared 5-methoxy-2-ethyl-1-phenyl-1H-benzo[g]indazol-3(2H)-one as a starting material, the title compound was synthesized according to the procedure described in (1) of Example 1.
Brownish yellow solid, Yield: 95%.
¹H NMR (300 MHz, DMSO-d₆) δ: 10.33 (br s, 1H), 8.24 (d, J=8.3 Hz, 1H), 7.57-7.50 (m, 4H), 7.38-7.34 (m, 3H), 7.30-7.27 (m, 1H), 7.02 (s, 1H), 3.58 (q, J=7.1 Hz, 2H), 1.10 (t, J=7.1 Hz, 3H).

(3) Synthesis of Compound 7 (2-ethyl-1-phenyl-1H-benzo[g]indazol-3,4,5 (2H)-trione)

Using the previously prepared 5-hydroxy-2-ethyl-1-phenyl-1H-benzo[g]indazol-3(2H)-one as a starting material, the title compound was synthesized according to the procedure described in (2) of Example 1.
Orange solid, Yield: 78%.
¹H NMR (300 MHz, DMSO-d₆) δ: 8.05 (d, J=7.7 Hz, 1H), 7.84-7.74 (m, 5H), 7.60 (t, J=7.6 Hz, 1H), 7.46 (t, J=7.8 Hz, 1H), 6.57 (d, J=7.9 Hz, 1H), 3.60 (q, J=7.0 Hz, 2H), 0.98 (t, J=7.0 Hz, 3H).

Example 8: Synthesis of Compound 8 (3-ethoxy-1-phenyl-1H-benzo[g]indazol-4,5-dione)

(1) Synthesis of 3-ethoxy-5-methoxy-1-phenyl-1H-benzo[g]indazole

Using Intermediate 2 as a starting material, the title compound was synthesized according to the procedure described in (1) of Example 7.
Pink solid, Yield: 79.4%.
¹H NMR (300 MHz, CDCl₃) δ: 8.35 (d, J=8.4 Hz, 1H), 7.57-7.47 (m, 7H), 7.34-7.30 (m, 1H), 6.95 (s, 1H), 4.50 (q, J=7.0 Hz, 2H), 4.06 (s, 3H), 1.52 (t, J=7.0 Hz, 3H).

(2) Synthesis of 3-ethoxy-1-phenyl-1H-benzo[g]indazol-5-ol

Using the previously prepared 3-ethoxy-5-methoxy-1-phenyl-1H-benzo[g]indazole as a starting material, the title compound was synthesized according to the procedure described in (1) of Example 1.
Orange solid, Yield: 82%.
¹H NMR (300 MHz, DMSO-d₆) δ: 9.97 (br s, 1H), 8.25 (d, J=8.4 Hz, 1H), 7.61-7.45 (m, 7H), 7.39-7.34 (m, 1H), 6.88 (s, 1H), 4.36 (q, J=7.0 Hz, 2H), 1.41 (t, J=7.0 Hz, 3H).

(3) Synthesis of Compound 8 (3-ethoxy-1-phenyl-1H-benzo[g]indazol-4,5-dione)

Using the previously prepared 3-ethoxy-1-phenyl-1H-benzo[g]indazol-5-ol as a starting material, the title compound was synthesized according to the procedure described in (2) of Example 1.
Yellow solid, Yield: 72%.
¹H NMR (300 MHz, DMSO-d₆) δ: 7.99 (d, J=7.3 Hz, 1H), 7.68-7.61 (m, 5H), 7.54-7.43 (m, 2H), 6.73 (d, J=7.7 Hz, 1H), 4.32 (q, J=7.0 Hz, 2H), 1.36 (t, J=7.0 Hz, 3H).

Example 9: Synthesis of Compound 9 (2-isobutyl-1-phenyl-1H-benzo[g]indazol-3,4,5(2H)-trione)

(1) Synthesis of 2-isobutyl-5-methoxy-1-phenyl-1H-benzo[g]indazol-3(2H)-one

Using 5-methoxy-2-methyl-1-phenyl-1H-benzo[g]indazol-3(2H)-one (1.00 mmol, Intermediate 2) and 1-iodo-2-methylpropane (5.01 mmol) as a starting material and a reactant, the title compound was synthesized according to the procedure described in (1) of Example 3.
White solid, Yield: 9.8%.
¹H NMR (300 MHz, DMSO-d₆) δ: 8.42 (d, J=8.4 Hz, 1H), 7.61-7.52 (m, 4H), 7.48-7.45 (m, 1H), 7.39-7.34 (m, 3H), 7.28 (s, 1H), 4.15 (s, 3H), 3.59 (d, J=7.5 Hz, 2H), 2.29-2.20 (m, 1H), 0.97 (d, J=6.6 Hz, 6H).

(2) Synthesis of 5-hydroxy-2-isobutyl-1-phenyl-1H-benzo[g]indazol-3(2H)-one

Using the previously prepared 2-isobutyl-5-methoxy-1-phenyl-1H-benzo[g]indazol-3(2H)-one as a starting material, the title compound was synthesized according to the procedure described in (1) of Example 1.

Yellow solid, Yield: 97%.

$^1$H NMR (300 MHz, DMSO-d$_6$) δ: 10.34 (br s, 1H), 8.24 (d, J=8.4 Hz, 1H), 7.56-7.50 (m, 4H), 7.39-7.30 (m, 4H), 7.03 (s, 1H), 3.37 (d, J=7.5 Hz, 2H), 2.03-1.99 (m, 1H), 0.77 (d, J=6.6 Hz, 6H).

(3) Synthesis of Compound 9 (2-isobutyl-1-phenyl-1H-benzo[g]indazol-3,4,5 (2H)-trione)

Using the previously prepared 5-hydroxy-2-isobutyl-1-phenyl-1H-benzo[g]indazol-3(2H)-one as a starting material, the title compound was synthesized according to the procedure described in (2) of Example 1.

Orange-red solid, Yield: 68%

$^1$H NMR (300 MHz, DMSO-d$_6$) δ: 8.05 (d, J=7.7 Hz, 1H), 7.83-7.72 (m, 5H), 7.60 (t, J=7.6 Hz, 1H), 7.45 (t, J=7.7 Hz, 1H), 6.58 (d, J=8.1 Hz, 1H), 3.41 (d, J=7.5 Hz, 2H), 1.56-1.52 (m, 1H), 0.71 (d, J=6.6 Hz, 6H).

Example 10: Synthesis of Compound 10 (3-isobutoxy-1-phenyl-1H-benzo[g]indazol-4,5-dione

(1) Synthesis of 3-isobutoxy-5-methoxy-1-phenyl-1H-benzo[g]indazole

Using Intermediate 2 as a starting material, the title compound was synthesized according to the procedure described in (1) of Example 9.

Yellowish white solid, Yield: 81.8%.

$^1$H NMR (300 MHz, CDCl$_3$) δ: 8.44 (d, J=8.4 Hz, 1H), 7.67-7.55 (m, 7H), 7.42-7.36 (m, 1H), 7.03 (s, 1H), 4.30 (d, J=6.6 Hz, 2H), 4.15 (s, 3H), 2.33-2.27 (m, 1H), 1.17 (d, J=6.8 Hz, 6H).

(2) Synthesis of 3-isobutoxy-1-phenyl-1H-benzo[g]indazol-5-ol

Using the previously prepared 3-isobutoxy-5-methoxy-1-phenyl-1H-benzo[g]indazole as a starting material, the title compound was synthesized according to the procedure described in (1) of Example 1.

Yellow solid, Yield: 84%.

$^1$H NMR (300 MHz, DMSO-d$_6$) δ: 9.96 (br s, 1H), 8.25 (d, J=8.0 Hz, 1H), 7.61-7.49 (m, 7H), 7.47-7.36 (m, 1H), 6.90 (s, 1H), 4.09 (d, J=6.6 Hz, 2H), 2.15-2.11 (m, 1H), 1.01 (d, J=6.6 Hz, 6H).

(3) Synthesis of Compound 10 (3-isobutoxy-1-phenyl-1H-benzo[g]indazol-4,5-dione)

Using the previously prepared 3-isobutoxy-1-phenyl-1H-benzo[g]indazol-5-ol as a starting material, the title compound was synthesized according to the procedure described in (2) of Example 1.

Yellow solid, Yield: 61%.

$^1$H NMR (300 MHz, DMSO-d$_6$) δ: 8.00 (d, J=6.2 Hz, 1H), 7.68-7.61 (m, 5H), 7.54-7.46 (m, 2H), 6.73 (d, J=7.7 Hz, 1H), 4.04 (d, J=6.6 Hz, 2H), 2.11-2.06 (m, 1H), 0.97 (d, J=6.6 Hz, 6H).

Example 11: Synthesis of Compound 11 (2-isopentyl-1-phenyl-1H-benzo[g]indazol-3,4,5(2H)-trione)

(1) Synthesis of 2-isopentyl-5-methoxy-1-phenyl-1H-benzo[g]indazol-3(2H)-one Using 5-methoxy-2-methyl-1-phenyl-1H-benzo[g]indazol-3(2H)-one (1.0 mmol, Intermediate 2) and 1-iodo-2-methylbutane (5.01 mmol) as a starting material and a reactant, the title compound was synthesized according to the procedure described in (1) of Example 3.

Yellow oil, Yield: 8.6%.

$^1$H NMR (300 MHz, DMSO-d$_6$) δ: 8.42 (d, J=8.4 Hz, 1H), 7.61-7.52 (m, 4H), 7.46-7.34 (m, 4H), 7.26 (s, 1H), 4.14 (s, 3H), 3.78 (t, J=7.2 Hz, 2H), 2.99 (d, J=20.9 Hz, 1H), 1.70-1.60 (m, 3H), 0.98 (d, J=6.2 Hz, 6H).

(2) Synthesis of 5-hydroxy-2-isopentyl-1-phenyl-1H-benzo[g]indazol-3(2H)-one Using the previously prepared 2-isopentyl-5-methoxy-1-phenyl-1H-benzo[g]indazol-3(2H)-one as a starting material, the title compound was synthesized according to the procedure described in (1) of Example 1.

Yellowish solid, Yield: 97%.

$^1$H NMR (300 MHz, DMSO-d$_6$) δ: 10.32 (br s, 1H), 8.24 (d, J=8.3 Hz, 1H), 7.56-7.51 (m, 4H), 7.36-7.28 (m, 4H), 7.01 (s, 1H), 3.59-3.56 (m, 2H), 1.45-1.42 (m, 3H), 0.82 (d, J=6.0 Hz, 6H).

(3) Synthesis of Compound 11 (2-isopentyl-1-phenyl-1H-benzo[g]indazol-3,4,5(2H)-trione)

Using the previously prepared 5-hydroxy-2-isopentyl-1-phenyl-1H-benzo[g]indazol-3(2H)-one as a starting material, the title compound was synthesized according to the procedure described in (2) of Example 1.

Yellowish orange solid, Yield: 64%.

$^1$H NMR (300 MHz, DMSO-d$_6$) δ: 8.05 (d, J=7.7 Hz, 1H), 7.84-7.73 (m, 5H), 7.60 (t, J=7.6 Hz, 1H), 7.46 (t, J=7.7 Hz, 1H), 6.59 (d, J=8.0 Hz, 1H), 3.59 (t, J=7.6 Hz, 2H), 1.44-1.37 (m, 1H), 1.26-1.18 (m, 2H), 0.72 (d, J=6.6 Hz, 6H).

Example 12: Synthesis of Compound 12 (3-(isopentyloxy)-1-phenyl-1H-benzo[g]indazol-4,5-dione)

(1) Synthesis of 3-(isopentyloxy)-5-methoxy-1-phenyl-1H-benzo[g]indazole

Using Intermediate 2 as a starting material, the title compound was synthesized according to the procedure described in (1) of Example 11.

Yellowish solid, Yield: 83.4%.

$^1$H NMR (300 MHz, CDCl$_3$) δ: 8.43 (d, J=8.4 Hz, 1H), 7.67-7.55 (m, 7H), 7.42-7.37 (m, 1H), 7.02 (s, 1H), 4.55 (t, J=6.8 Hz, 2H), 4.14 (s, 3H), 2.02-1.97 (m, 1H), 1.91-1.85 (m, 2H), 1.09 (d, J=6.4 Hz, 6H).

(2) Synthesis of 3-(isopentyloxy)-1-phenyl-1H-benzo[g]indazol-5-ol

Using the previously prepared 3-(isopentyloxy)-5-methoxy-1-phenyl-1H-benzo[g]indazole as a starting material, the title compound was synthesized according to the procedure described in (1) of Example 1.

Yellow solid, Yield: 80%

$^1$H NMR (300 MHz, DMSO-d$_6$) δ: 9.95 (br s, 1H), 8.25 (d, J=7.9 Hz, 1H), 7.61-7.44 (m, 7H), 7.39-7.34 (m, 1H), 6.88 (s, 1H), 4.35 (t, J=6.5 Hz, 2H), 1.84-1.67 (m, 3H), 0.95 (d, J=6.6 Hz, 6H).

(3) Synthesis of Compound 12 (3-(isopentyloxy)-1-phenyl-1H-benzo[g]indazol-4,5-dione)

Using the previously prepared 3-(isopentyloxy)-1-phenyl-1H-benzo[g]indazol-5-ol as a starting material, the title compound was synthesized according to the procedure described in (2) of Example 1.

Orange-red solid, Yield: 64%.

$^1$H NMR (300 MHz, DMSO-$d_6$) δ: 7.99 (d, J=7.7 Hz, 1H), 7.68-7.60 (m, 5H), 7.54-7.43 (m, 2H), 6.71 (d, J=7.5 Hz, 1H), 4.30 (t, J=6.6 Hz, 2H), 1.78-1.62 (m, 3H), 0.92 (d, J=6.4 Hz, 6H).

Example 13: Synthesis of Compound 13 (2-isopropyl-1-phenyl-1H-benzo[g]indazol-3,4,5(2H)-trione)

(1) Synthesis of 1-bromo-N-isopropyl-4-methoxy-N'-phenyl-2-naphthohydrazide

Using 1-bromo-4-methoxy-2-naphthoic acid (1.70 mmol, Intermediate 1) and 1-isopropyl-2-phenylhydrazine hydrochloride (1.75 mmol, Intermediate 4) as a starting material and a reactant in a dried round bottom flask under argon atmosphere, the title compound was synthesized according to the procedure described in (1) of Preparation Example 3.

Yellow oil, Yield: 68%.

$^1$H NMR (300 MHz, CDCl$_3$) δ: 8.31-8.09 (m, 2H), 7.61-7.44 (m, 2H), 7.13-6.97 (m, 3H), 6.72-7.68 (m, 1H), 6.54-6.51 (m, 1H), 6.41 (s, 1H), 5.90 (s, 1H), 5.08-5.06 (m, 1H), 3.66 (s, 3H), 1.26 (m, 6H).

(2) Synthesis of 2-isopropyl-5-methoxy-1-phenyl-1H-benzo[g]indazol-3(2H)-one

Using the previously prepared 1-bromo-N-isopropyl-4-methoxy-N'-phenyl-2-naphthohydrazide (1.16 mmol) as a starting material, the title compound was synthesized according to the procedure described in (2) of Preparation Example 2.

Yellow oil, Yield: 53%.

$^1$H NMR (300 MHz, DMSO-$d_6$) δ: 8.24 (d, J=8.4 Hz, 1H), 7.60-7.50 (m, 4H), 7.44-7.38 (m, 4H), 7.06 (s, 1H), 4.24 (m, 1H), 4.03 (s, 3H), 1.24 (d, J=6.8 Hz, 6H).

(3) Synthesis of 5-hydroxy-2-isopropyl-1-phenyl-1H-benzo[g]indazol-3(2H)-one

Using the previously prepared 2-isopropyl-5-methoxy-1-phenyl-1H-benzo[g]indazol-3(2H)-one as a starting material, the title compound was synthesized according to the procedure described in (1) of Example 1.

Purple-white solid, Yield: 95%.

$^1$H NMR (300 MHz, DMSO-$d_6$) δ: 10.30 (br s, 1H), 8.22 (d, J=8.4 Hz, 1H), 7.55-7.48 (m, 4H), 7.42-7.34 (m, 4H), 6.98 (s, 1H), 4.22-4.20 (m, 1H), 1.22 (d, J=6.8 Hz, 6H).

(4) Synthesis of Compound 13 (2-isopropyl-1-phenyl-1H-benzo[g]indazol-3,4,5(2H)-trione)

Using the previously prepared 5-hydroxy-2-isopropyl-1-phenyl-1H-benzo[g]indazol-3(2H)-one (0.52 mmol) as a starting material, the title compound was synthesized according to the procedure described in (2) of Example 1.

Yellow solid, Yield: 77%.

$^1$H NMR (300 MHz, DMSO-$d_6$) δ: 8.03 (d, J=7.9 Hz, 1H), 7.81-7.75 (m, 5H), 7.59 (t, J=7.1 Hz, 1H), 7.43 (t, J=7.0 Hz, 1H), 6.52 (d, J=7.3 Hz, 1H), 3.89-3.87 (m, 1H), 1.34-1.31 (d, J=6.8 Hz, 6H).

Example 14: Synthesis of Compound 14 (2-methyl-3-phenyl-2,3-dihydro-1H-benzo[e]indazol-1,4,5-trione)

(1) Synthesis of 5-methoxy-2-methyl-3-phenyl-2,3-dihydro-1H-benzo[e]indazol-1-one Using Intermediate 5 as a starting material, the title compound was synthesized according to the procedure described in (1) of Example 3.

Yellowish solid, Yield: 28%.

$^1$H NMR (300 MHz, CDCl$_3$) δ: 8.98 (d, J=8.1 Hz, 1H), 8.20 (d, J=8.3 Hz, 1H), 7.71-7.66 (m, 1H), 7.56-7.51 (m, 2H), 7.48-7.43 (m, 2H), 7.36-7.33 (m, 2H), 6.35 (s, 1H), 3.92 (s, 3H), 3.33 (s, 3H).

(2) Synthesis of 5-hydroxy-2-methyl-3-phenyl-2,3-dihydro-1H-benzo[e]indazol-1-one Using the previously prepared 5-methoxy-2-methyl-3-phenyl-2,3-dihydro-1H-benzo[e]indazol-1-one as a starting material, the title compound was synthesized according to the procedure described in (1) of Example 1.

Pale-yellow solid, Yield: 85.8%.

$^1$H NMR (300 MHz, DMSO-$d_6$) δ: 11.00 (br s, 1H), 8.76 (d, J=8.3 Hz, 1H), 8.12 (d, J=8.4 Hz, 1H), 7.69-7.64 (m, 1H), 7.61-7.56 (m, 2H), 7.48-7.40 (m, 4H), 6.56 (s, 1H), 3.19 (s, 3H).

(3) Synthesis of Compound 14 (2-methyl-3-phenyl-2,3-dihydro-1H-benzo[e]indazol-1,4,5-trione)

Using the previously prepared 5-hydroxy-2-methyl-3-phenyl-2,3-dihydro-1H-benzo[e]indazol-1-one as a starting material, the title compound was synthesized according to the procedure described in (2) of Example 1.

Dark-purple solid, Yield: 91%

$^1$H NMR (300 MHz, CDCl$_3$) δ: 8.57 (d, J=7.7 Hz, 1H), 8.03 (d, J=7.9 Hz, 1H), 7.65 (td, J=7.6, 1.4 Hz, 1H), 7.56-7.52 (m, 3H), 7.37-7.32 (m, 3H), 3.30 (s, 3H).

Example 15: Synthesis of Compound 15 (1-methoxy-3-phenyl-3H-benzo[e]indazol-4,5-dione)

(1) Synthesis of 1,5-dimethoxy-3-phenyl-3H-benzo[e]indazole

Using Intermediate 5 as a starting material, the title compound was synthesized according to the procedure described in (1) of Example 14.

White solid, Yield: 51%.

$^1$H NMR (300 MHz, CDCl$_3$) δ: 8.48 (d, J=7.5 Hz, 1H), 8.26 (d, J=7.7 Hz, 1H), 7.73-7.69 (m, 2H), 7.66-7.61 (m, 1H), 7.56-7.51 (m, 2H), 7.47-7.42 (m, 1H), 7.36-7.31 (m, 1H), 6.95 (s, 1H), 4.24 (s, 3H), 4.02 (s, 3H).

(2) Synthesis of 1-methoxy-3-phenyl-3H-benzo[e]indazol-5-ol

Using the previously prepared 1,5-dimethoxy-3-phenyl-3H-benzo[e]indazole as a starting material, the title compound was synthesized according to the procedure described in (1) of Example 1. The resulting pale-yellow product was used for the next step without column chromatography purification.

(3) Synthesis of Compound 15 (1-methoxy-3-phenyl-3H-benzo[e]indazol-4,5-dione)

Using the previously prepared 1-methoxy-3-phenyl-3H-benzo[e]indazol-5-ol as a starting material, the title compound was synthesized according to the procedure described in (2) of Example 1.

Red solid, Yield: 40%

$^1$H NMR (300 MHz, CDCl$_3$) δ: 8.07 (d, J=7.9 Hz, 1H), 8.01 (d, J=7.9 Hz, 1H), 7.64 (td, J=7.7, 1.3 Hz, 1H), 7.43-7.29 (m, 4H), 7.11-7.08 (m, 1H), 7.03-7.00 (m, 1H), 4.18 (s, 3H).

Example 16: Synthesis of Compound 16 (1-isopropyl-2-methyl-1H-benzo[g]indazol-3,4,5(2H)-trione)

(1) Synthesis of 1-isopropyl-5-methoxy-2-methyl-1H-benzo[g]indazol-3(2H)-one Using 1-isopropyl-5-methoxy-1H-benzo[g]indazol-3(2H)-one (1.00 mmol, Intermediate 7) as a starting material, the title compound was synthesized according to the procedure described in (1) of Example 3.

Brown solid, Yield: 33%

$^1$H NMR (300 MHz, DMSO-d$_6$) δ: 8.32-8.29 (m, 1H), 8.10-8.07 (m, 1H), 7.74-7.67 (m, 2H), 6.99 (s, 1H), 4.53-4.96 (m, 1H), 4.00 (s, 3H), 3.45 (s, 3H), 1.19 (d, J=6.8 Hz, 6H).

(2) Synthesis of 5-hydroxy-1-isopropyl-2-methyl-1H-benzo[g]indazol-3(2H)-one Using the previously prepared 1-isopropyl-5-methoxy-2-methyl-1H-benzo[g]indazol-3(2H)-one as a starting material, the title compound was synthesized according to the procedure described in (1) of Example 1.

Greenish solid, Yield: 70%.

$^1$H NMR (300 MHz, DMSO-d$_6$) δ: 10.27 (br s, 1H), 8.31-8.27 (m, 1H), 8.06-8.03 (m, 1H), 7.71-7.63 (m, 2H), 6.90 (s, 1H), 4.49-4.45 (m, 1H), 3.43 (s, 3H), 1.17 (d, J=6.8 Hz, 6H).

(3) Synthesis of Compound 16 (1-isopropyl-2-methyl-1H-benzo[g]indazol-3,4,5(2H)-trione)

Using the previously prepared 5-hydroxy-1-isopropyl-2-methyl-1H-benzo[g]indazol-3(2H)-one as a starting material, the title compound was synthesized according to the procedure described in (2) of Example 1.

Orange solid, Yield: 60%.

$^1$H NMR (300 MHz, DMSO-d$_6$) δ: 8.09-8.07 (m, 1H), 7.88-7.86 (m, 1H), 7.80-7.73 (m, 2H), 4.99-4.97 (m, 1H), 3.46 (s, 3H), 1.53 (d, J=6.8 Hz, 6H).

Example 17: Synthesis of Compound 17 (1-isopropyl-3-methoxy-1H-benzo[g]indazol-4,5-dione)

(1) Synthesis of 1-isopropyl-3,5-dimethoxy-1H-benzo[g]indazole

Using Intermediate 7 as a starting material, the title compound was synthesized according to the procedure described in (1) of Example 16.

Yellowish solid, Yield: 65%.

$^1$H NMR (300 MHz, CDCl$_3$) δ: 8.45 (d, J=8.3 Hz, 1H), 8.30 (d, J=8.3 Hz, 1H), 7.73-7.61 (m, 2H), 6.90 (s, 1H), 5.39-5.30 (m, 2H), 4.03 (s, 3H), 3.97 (s, 3H), 1.52 (d, J=6.4 Hz, 6H).

(2) Synthesis of 1-isopropyl-3-methoxy-1H-benzo[g]indazol-5-ol

Using the previously prepared 1-isopropyl-3,5-dimethoxy-1H-benzo[g]indazole as a starting material, the title compound was synthesized according to the procedure described in (1) of Example 1.

Yellow solid, Yield: 82%.

$^1$H NMR (300 MHz, DMSO-d$_6$) δ: 9.73 (br s, 1H), 8.42-8.39 (m, 1H), 8.31-8.28 (m, 1H), 7.68-7.59 (m, 2H), 6.82 (s, 1H), 5.36-5.27 (m, 1H), 4.00 (s, 3H), 1.50 (d, J=6.4 Hz, 6H).

(3) Synthesis of Compound 17 (1-isopropyl-3-methoxy-1H-benzo[g]indazol-4,5-dione)

Using the previously prepared 1-isopropyl-3-methoxy-1H-benzo[g]indazol-5-ol as a starting material, the title compound was synthesized according to the procedure described in (2) of Example 1.

Red solid, Yield: 42%

$^1$H NMR (300 MHz, CDCl$_3$) δ: 8.07-8.03 (m, 2H), 7.85-7.79 (m, 1H), 7.65-7.60 (m, 1H), 5.22-5.14 (m, 1H), 3.96 (s, 3H), 1.53 (d, J=6.4 Hz, 6H).

Example 18: Synthesis of Compound 18 (3-methoxy-1-(4-(trifluoromethyl)phenyl)-1H-benzo[g]indazol-4,5-dione)

(1) Synthesis of 3,5-dimethoxy-1-(4-(trifluoromethyl)phenyl)-1H-benzo[g]indazole Using Intermediate 8 as a starting material, the title compound was synthesized according to the procedure described in (1) of Example 3.

Yellowish solid, Yield: 78%.

$^1$H NMR (300 MHz, CDCl$_3$) δ: 8.33-8.30 (m, 1H), 7.97-7.94 (m, 2H), 7.83-7.80 (m, 2H), 7.65-7.60 (m, 2H), 7.55-7.49 (m, 1H), 7.03 (s, 1H), 4.07 (s, 3H), 4.03 (s, 3H).

(2) Synthesis of 3-methoxy-1-(4-(trifluoromethyl)phenyl)-1H-benzo[g]indazol-5-ol Using the previously prepared 3,5-dimethoxy-1-(4-(trifluoromethyl)phenyl)-1H-benzo[g]indazole as a starting material, the title compound was synthesized according to the procedure described in (1) of Example 1.

White solid, Yield: 99%.

$^1$H NMR (300 MHz, DMSO-d$_6$) δ: 10.16 (br s, 1H), 8.33-8.30 (m, 1H), 7.95-7.93 (m, 2H), 7.81-7.78 (m, 2H), 7.62-7.57 (m, 2H), 7.51-7.46 (m, 1H), 6.93 (s, 1H), 4.05 (s, 3H).

(3) Synthesis of Compound 18 (3-methoxy-1-(4-(trifluoromethyl)phenyl)-1H-benzo[g]indazol-4,5-dione)

Using the previously prepared 3-methoxy-1-(4-(trifluoromethyl)phenyl)-1H-benzo[g]indazol-5-ol as a starting material, the title compound was synthesized according to the procedure described in (2) of Example 1.

Yellow solid, Yield: 75%.

¹H NMR (300 MHz, CDCl₃) δ: 8.08-8.02 (m, 3H), 7.93-7.90 (m, 2H), 7.57-7.53 (m, 2H), 6.88-6.85 (m, 1H), 3.98 (s, 3H).

Example 19: Synthesis of Compound 19 (1-(4-fluorophenyl)-3-methoxy-1H-benzo[g]indazol-4,5-dione)

(1) Synthesis of 1-(4-fluorophenyl)-3,5-dimethoxy-1H-benzo[g]indazole

Using Intermediate 9 as a starting material, the title compound was synthesized according to the procedure described in (1) of Example 3.
Yellowish solid, Yield: 42%
¹H NMR (300 MHz, CDCl₃) δ: 8.30-8.27 (m, 1H), 7.64-7.58 (m, 3H), 7.45-7.41 (m, 4H), 7.00 (s, 1H), 4.05 (s, 3H), 4.02 (s, 3H).

(2) Synthesis of 1-(4-fluorophenyl)-3-methoxy-1H-benzo[g]indazol-5-ol

Using the previously prepared 1-(4-fluorophenyl)-3,5-dimethoxy-1H-benzo[g]indazole as a starting material, the title compound was synthesized according to the procedure described in (1) of Example 1.
White solid, Yield: 50%.
¹H NMR (300 MHz, DMSO-d₆) δ: 10.03 (br s, 1H), 8.29-8.26 (m, 1H), 7.62-7.53 (m, 3H), 7.46-7.40 (m, 4H), 6.90 (s, 1H), 4.02 (s, 3H).

(3) Synthesis of Compound 19 (1-(4-fluorophenyl)-3-methoxy-1H-benzo[g]indazol-4,5-dione)

Using the previously prepared 1-(4-fluorophenyl)-3-methoxy-1H-benzo[g]indazol-5-ol as a starting material, the title compound was synthesized according to the procedure described in (2) of Example 1.
Yellow solid, Yield: 53%.
¹H NMR (300 MHz, CDCl₃) δ: 8.04-8.01 (m, 1H), 7.75-7.71 (m, 2H), 7.56-7.50 (m, 4H), 6.79-6.76 (m, 1H), 3.97 (s, 3H).

Example 20: Synthesis of Compound 20 (1-methyl-2-phenyl-1H-benzo[g]indazol-3,4,5(2H)-trione)

(1) Synthesis of 5-methoxy-1-methyl-2-phenyl-1H-benzo[g]indazol-3(2H)-one

Using Intermediate 10 as a starting material, the title compound was synthesized according to the procedure described in (1) of Example 3.
Light-brown solid, Yield: 90%.
¹H NMR (300 MHz, CDCl₃) δ: 8.39-8.34 (m, 2H), 7.83-7.72 (m, 4H), 7.60-7.55 (m, 2H), 7.37-7.32 (m, 1H), 7.10 (s, 1H), 4.06 (s, 3H), 3.27 (s, 3H).

(2) Synthesis of 5-hydroxy-1-methyl-2-phenyl-1H-benzo[g]indazol-3(2H)-one

Using the previously prepared 5-methoxy-1-methyl-2-phenyl-1H-benzo[g]indazol-3(2H)-one as a starting material, the title compound was synthesized according to the procedure described in (1) of Example 1.
Light-brown solid, Yield: 95%.
¹H NMR (300 MHz, DMSO-d₆) δ: 10.44 (br s, 1H), 8.37-8.28 (m, 2H), 7.78-7.71 (m, 4H), 7.59-7.54 (m, 2H), 7.35-7.30 (m, 1H), 7.01 (s, 1H), 3.27 (s, 3H).

(3) Synthesis of Compound 20 (1-methyl-2-phenyl-1H-benzo[g]indazol-3,4,5 (2H)-trione)

Using the previously prepared 5-hydroxy-1-methyl-2-phenyl-1H-benzo[g]indazol-3(2H)-one as a starting material, the title compound was synthesized according to the procedure described in (2) of Example 1.
Yellow solid, Yield: 43%.
¹H NMR (300 MHz, CDCl₃) δ: 8.19-8.14 (m, 2H), 7.95-7.89 (m, 1H), 7.83-7.78 (m, 1H), 7.65-7.59 (m, 2H), 7.54-7.49 (m, 3H), 3.84 (s, 3H).

Example 21: Synthesis of Compound 21 (7-fluoro-2-methyl-1-phenyl-1H-benzo[g]indazol-3,4,5(2H)-trione)

(1) Synthesis of 7-fluoro-5-methoxy-2-methyl-1-phenyl-1H-benzo[g]indazol-3(2H)-one Using 7-fluoro-5-methoxy-1-phenyl-1H-benzo[g]indazol-3(2H)-one (1.5 mmol, Intermediate 12) as a starting material, the title compound was synthesized according to the procedure described in (1) of Example 3.
Light-brown solid, Yield: 35%.
¹H NMR (300 MHz, DMSO-d₆) δ: 7.92-7.88 (m, 1H), 7.58-7.56 (m, 3H), 7.42-7.29 (m, 4H), 7.19 (s, 1H), 4.06 (s, 3H), 3.18 (s, 3H).

(2) Synthesis of 7-fluoro-5-hydroxy-2-methyl-1-phenyl-1H-benzo[g]indazol-3(2H)-one Using the previously prepared 7-fluoro-5-methoxy-2-methyl-1-phenyl-1H-benzo[g]indazol-3(2H)-one as a starting material, the title compound was synthesized according to the procedure described in (1) of Example 1.
Yellow solid, Yield: 90%.
¹H NMR (300 MHz, DMSO-d₆) δ: 10.50 (br s, 1H), 7.90-7.86 (m, 1H), 7.56-7.54 (m, 3H), 7.38-7.30 (m, 4H), 7.08 (s, 1H), 3.15 (s, 3H).

(3) Synthesis of Compound 21 (7-fluoro-2-methyl-1-phenyl-1H-benzo[g]indazol-3,4,5(2H)-trione)

Using the previously prepared 7-fluoro-5-hydroxy-2-methyl-1-phenyl-1H-benzo[g]indazol-3(2H)-one as a starting material, the title compound was synthesized according to the procedure described in (2) of Example 1.
Red solid, Yield: 60%.
¹H NMR (300 MHz, DMSO-d₆) δ: 7.85-7.74 (m, 6H), 7.43-7.37 (m, 1H), 6.63-6.56 (m, 1H), 3.07 (s, 3H).

Example 22: Synthesis of Compound 22 (7-fluoro-3-methoxy-1-phenyl-1H-benzo[g]indazol-4,5-dione)

(1) Synthesis of 7-fluoro-3,5-dimethoxy-1-phenyl-1H-benzo[g]indazole

Using Intermediate 12 as a starting material, the title compound was synthesized according to the procedure described in (1) of Example 21.
Light-brown solid, Yield: 56%.

¹H NMR (300 MHz, CDCl₃) δ: 7.93-7.89 (m, 1H), 7.70-7.49 (m, 6H), 7.41-7.34 (m, 1H), 7.08 (s, 1H), 4.05 (s, 3H), 4.02 (s, 3H).

(2) Synthesis of 7-fluoro-3-methoxy-1-phenyl-1H-benzo[g]indazol-5-ol

Using the previously prepared 7-fluoro-3,5-dimethoxy-1-phenyl-1H-benzo[g]indazole as a starting material, the title compound was synthesized according to the procedure described in (1) of Example 1.

Yellowish white solid, Yield: 98%.

¹H NMR (300 MHz, DMSO-d₆) δ: 10.19 (br s, 1H), 7.92-7.87 (m, 1H), 7.64-7.48 (m, 6H), 7.37-7.30 (m, 1H), 6.96 (s, 1H), 4.02 (s, 3H).

(3) Synthesis of Compound 22 (7-fluoro-3-methoxy-1-phenyl-1H-benzo[g]indazol-4,5-dione)

Using the previously prepared 7-fluoro-3-methoxy-1-phenyl-1H-benzo[g]indazol-5-ol as a starting material, the title compound was synthesized according to the procedure described in (2) of Example 1.

Yellow solid, Yield: 92%.

¹H NMR (300 MHz, DMSO-d₆) δ: 7.76-7.63 (m, 5H), 7.44-7.37 (m, 1H), 7.24-7.12 (m, 1H), 6.80-6.75 (m, 1H), 3.97 (s, 3H).

Example 23: Synthesis of Compound 23 (3-methoxy-7-nitro-1-phenyl-1H-benzo[g]indazol-4,5-dione)

(1) Synthesis of 3,5-dimethoxy-7-nitro-1-phenyl-1H-benzo[g]indazole

Using Intermediate 14 as a starting material, the title compound was synthesized according to the procedure described in (1) of Example 3.

Yellow solid, Yield: 70%.

¹H NMR (300 MHz, CDCl₃) δ: 9.07-9.06 (m, 1H), 8.24-8.20 (m, 1H), 7.67-7.60 (m, 6H), 7.21 (s, 1H), 4.09 (s, 3H), 4.08 (s, 3H).

(2) Synthesis of 3-methoxy-7-nitro-1-phenyl-1H-benzo[g]indazol-5-ol

Using the previously prepared 3,5-dimethoxy-7-nitro-1-phenyl-1H-benzo[g]indazole as a starting material, the title compound was synthesized according to the procedure described in (1) of Example 1.

Orange solid, Yield: 62%.

¹H NMR (300 MHz, DMSO-d₆) δ: 10.74 (br s, 1H), 9.11-9.10 (m, 1H), 8.21-8.17 (m, 1H), 7.68-7.56 (m, 6H), 7.08 (s, 1H), 4.05 (s, 3H).

(3) Synthesis of Compound 23 (3-methoxy-7-nitro-1-phenyl-1H-benzo[g]indazol-4,5-dione)

Using the previously prepared 3-methoxy-7-nitro-1-phenyl-1H-benzo[g]indazol-5-ol as a starting material, the title compound was synthesized according to the procedure described in (2) of Example 1.

Yellow solid, Yield: 74%.

¹H NMR (300 MHz, DMSO-d₆) δ: 8.60-8.59 (m, 1H), 8.34-8.31 (m, 1H), 7.76-7.63 (m, 5H), 7.01-6.98 (m, 1H), 4.00 (s, 3H).

Example 24: Synthesis of Compound 24 (7-amino-3-methoxy-1-phenyl-1H-benzo[g]indazol-4,5-dione)

3-Methoxy-7-nitro-1-phenyl-1H-benzo[g]indazol-4,5-dione (0.29 mmol, Compound 23) was put into a round bottom flask and replaced under reduced pressure with hydrogen gas, to which 10% Pd/C (10 wt %) was added, and then methanol (5 mL) and dichloromethane (5 mL) were added to dissolve the reaction mixture. After reacting under a hydrogen atmosphere for 2 hours, the reaction mixture was filtered through Celite pad, and filtrate was concentrated under reduced pressure. The crude product was recrystallized with ethyl acetate to yield the title compound.

Purple solid, Yield: 79%.

¹H NMR (300 MHz, DMSO-d₆) δ: 7.66-7.57 (m, 5H), 7.22-7.21 (m, 1H), 6.50-6.39 (m, 2H), 6.07 (br s, 2H), 3.92 (s, 3H).

Example 25: Synthesis of Compound 25 (7-bromo-3-methoxy-1-phenyl-1H-benzo[g]indazol-4,5-dione)

(1) Synthesis of 7-bromo-3,5-dimethoxy-1-phenyl-1H-benzo[g]indazole

Using Intermediate 16 as a starting material, the title compound was synthesized according to the procedure described in (1) of Example 3.

Light-brown solid, Yield: 71%.

¹H NMR (300 MHz, CDCl₃) δ: 8.40-8.39 (m, 1H), 7.64-7.56 (m, 6H), 7.43-7.40 (m, 1H), 7.08 (s, 1H), 4.05 (s, 3H), 4.02 (s, 3H).

(2) Synthesis of 7-bromo-3-methoxy-1-phenyl-1H-benzo[g]indazol-5-ol

Using the previously prepared 7-bromo-3,5-dimethoxy-1-phenyl-1H-benzo[g]indazole as a starting material, the title compound was synthesized according to the procedure described in (1) of Example 1.

Orange solid, Yield: 96%.

¹H NMR (300 MHz, DMSO-d₆) δ: 10.27 (br s, 1H), 8.38 (s, 1H), 7.58-7.56 (m, 5H), 7.74-7.38 (m, 1H), 6.96 (s, 1H), 4.02 (s, 3H).

(3) Synthesis of Compound 25 (7-bromo-3-methoxy-1-phenyl-1H-benzo[g]indazol-4,5-dione)

Using the previously prepared 7-bromo-3-methoxy-1-phenyl-1H-benzo[g]indazol-5-ol as a starting material, the title compound was synthesized according to the procedure described in (2) of Example 1.

Yellow solid, Yield: 50%.

¹H NMR (300 MHz, DMSO-d₆) δ: 8.05 (s, 1H), 7.74-7.60 (m, 7H), 6.67-6.64 (d, J=8.6 Hz, 1H), 3.97 (s, 3H).

EXPERIMENTAL EXAMPLE

Experimental Example 1: In Vitro NQO1 Enzyme Activity Assay

In order to evaluate the activity of synthesized compound in NQO1, the experiments were conducted as follows:

The synthesized compound was dissolved in DMSO to make a 10 mM stock solution, which was further diluted with DMSO to 250 μM so as to prepare a working solution. For experimental groups, the working solution of the compound was added to an enzyme reaction solution in which 50

μL of 1.54 mM Cytochrome C solution was added to 900 μL of 50 mM Tris-HCl (pH7.5) containing 0.14% BSA. For negative control groups, DMSO not containing the compound of the invention was added to the enzyme reaction solution as above. For each experimental and control group, 20 μL of 100 ng/mL NQO1 protein was added. Next, 10 μL of 20 mM NADH was added to bring up the volume to 1 mL. The change of absorbance was measured at 550 nm for 10 minutes using 1 mL cuvette. The kinetics of reaction was measured with the increase of absorbance as the cytochrome C was reduced at 550 nm over 10 minutes. The activity of NQO1 was measured by the amount of cytochrome C that is being reduced (nmol cytochrome C that was reduced/min/ug NQO1 protein).

Absorption coefficient of Cytochrome C: 21.1 (μmol/mL)$^{-1}$ cm$^{-1}$

BSA: Bovine Serum Albumin

Tris-HCl: Tris(hydroxymethyl)aminomethane hydrochloride (buffer solution)

Equipment=Cary 100 UV-Vis Spectrophotometer

The results are shown in Tables 1 to 4.

TABLE 1

NQO1 activity (5 μM of Compound, nmol of reduced Cytochrome C/min/μg NQO1 protein)

| Compounds | NQO1 2 ng, Compound 5 μM |
|---|---|
| Control | 196 |
| 1 | 180 |
| 3 | 3066 |
| 5 | 2602 |
| 6 | 7706 |

TABLE 2

NQO1 activity (0.2 μM of Compound, nmol of reduced Cytochrome C/min/μg NQO1 protein)

| Compounds | NQO1 2 ng, Compound 0.2 μM |
|---|---|
| Control | 96 |
| 2 | 3531 |
| 6 | 3782 |
| 7 | 2246 |
| 8 | 3768 |
| 9 | 2474 |
| 10 | 3455 |
| 11 | 2839 |
| 12 | 2981 |
| 13 | 2137 |
| 16 | 4441 |
| 18 | 4232 |
| 19 | 4303 |

TABLE 3

NQO1 activity (0.2 μM of compound, nmol of reduced Cytochrome C/min/μg NQO1 protein)

| Compounds | NQO1 2 ng, Compound 0.2 μM |
|---|---|
| Control | 74 |
| 6 | 2905 |
| 17 | 4488 |
| 20 | 436 |
| 21 | 1095 |
| 22 | 5360 |

TABLE 4

NQO1 activity (0.2 μM of compound, nmol of reduced Cytochrome C/min/μg NQO1 protein)

| Compounds | NQO1 2 ng, Compound 0.2 μM |
|---|---|
| Control | 10 |
| 6 | 3261 |
| 23 | 393 |
| 24 | 3739 |
| 25 | 1445 |

As shown in Tables 1 to 4, the amount of cytochrome C being reduced was increased when treated with the compound of the invention, compared with the control not treated with the compound, by which it was found that the compound of the invention was used as a substrate for NQO1 to activate redox reaction of NQO1.

The invention claimed is:

1. A compound of Chemical Formula 1, or a pharmaceutically acceptable salt, hydrate, solvate, enantiomer, diastereomer, tautomer or prodrug thereof:

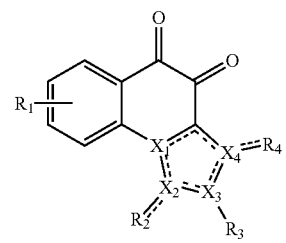

Chemical Formula 1 wherein:
$R_1$ is selected from the group consisting of H, $C_{1-6}$ alkyl, $C_{1-6}$ alkoxy, substituted or unsubstituted $C_{6-10}$ aryl, substituted or unsubstituted heteroaryl, halo, cyano, nitro and $NR_5R_6$;
$R_2$ and $R_3$ are each independently not present, or selected from the group consisting of H, O, $C_{1-6}$ alkyl, substituted or unsubstituted $C_{6-10}$ aryl and $C_{1-6}$ alkoxy; and
$R_4$ is selected from the group consisting of O, unsubstituted $C_{6-10}$ aryl and $C_{1-6}$ alkoxy, wherein at least one of $R_2$ and $R_4$ are O or $C_{1-6}$ alkoxy;
$R_5$ and $R_6$ are each independently H, $C_{1-6}$ alkyl or $C_{1-6}$ alkyl carbonyl, or $R_5$ and $R_6$ may be joined together to form a heterocyclyl containing at least one nitrogen atom in ring structure;
$X_1$, $X_2$, $X_3$ and $X_4$ are each independently selected from C and N, wherein two of $X_1$, $X_2$, $X_3$ and $X_4$ are N, provided that $X_2$ and $X_4$ are not simultaneously N, and $X_1$ and $X_4$ are not simultaneously N;
⸺ is a single bond or a double bond depending on $R_2$, $R_3$, $R_4$, $X_1$, $X_2$, $X_3$ and $X_4$;
wherein the alkyl is a linear, branched or cyclic alkyl, the heteroaryl is a 5- to 10-membered aromatic ring containing at least one hetero atom selected from the group consisting of N, O and S in the ring, and where the aryl or heteroaryl is substituted, a substituent thereof is $C_{1-6}$ alkyl, halo, or $C_{1-6}$ alkyl substituted with 1 to 3 halos.

2. The compound according to claim 1, or a pharmaceutically acceptable salt, hydrate, solvate, enantiomer, diastereomer, tautomer or prodrug thereof, wherein at least one of $R_2$, $R_3$ and $R_4$ is $C_{1-6}$ alkoxy.

3. The compound according to claim 1, or a pharmaceutically acceptable salt, hydrate, solvate, enantiomer, diasteromer, tautomer or prodrug thereof, wherein at least one of bonds between $R_2$ and $X_2$, $R_3$ and $X_3$, and $R_4$ and $X_4$ is C=O.

4. The compound according to claim 1, or a pharmaceutically acceptable salt, hydrate, solvate, enantiomer, diasteromer, tautomer or prodrug thereof, wherein at least two of ≡≡≡ are double bonds.

5. The compound according to claim 1, or a pharmaceutically acceptable salt, hydrate, solvate, enantiomer, diasteromer, tautomer or prodrug thereof, wherein $X_1$ and $X_4$ are C, and $X_2$ and $X_3$ are N.

6. The compound according to claim 5, or a pharmaceutically acceptable salt, hydrate, solvate, enantiomer, diasteromer, tautomer or prodrug thereof, wherein $R_4$ is $C_{1-6}$ alkoxy.

7. The compound according to claim 5, or a pharmaceutically acceptable salt, hydrate, solvate, enantiomer, diasteromer, tautomer or prodrug thereof, wherein the bond between $R_4$ and $X_4$ is C=O.

8. The compound according to claim 1, or a pharmaceutically acceptable salt, hydrate, solvate, enantiomer, diasteromer, tautomer or prodrug thereof, wherein $X_1$ and $X_2$ are C, and $X_3$ and $X_4$ are N.

9. The compound according to claim 8, or a pharmaceutically acceptable salt, hydrate, solvate, enantiomer, diasteromer, tautomer or prodrug thereof, wherein $R_2$ is $C_{1-6}$ alkoxy.

10. The compound according to claim 8, or a pharmaceutically acceptable salt, hydrate, solvate, enantiomer, diasteromer, tautomer or prodrug thereof, wherein the bond between $R_2$ and $X_2$ is C=O.

11. The compound according to claim 1, or a pharmaceutically acceptable salt, hydrate, solvate, enantiomer, diasteromer, tautomer or prodrug thereof, wherein $X_2$ and $X_3$ are C, and $X_1$ and $X_3$ are N.

12. The compound according to claim 1, or a pharmaceutically acceptable salt, hydrate, solvate, enantiomer, diasteromer, tautomer or prodrug thereof, wherein the compound is selected from the group consisting of:
1-phenyl-1H-benzo[g]indazol-3,4,5(2H)-trione;
3-isopropoxy-1-phenyl-1H-benzo[g]indazol-4,5-dione;
2-isopropyl-1-methyl-1H-benzo[g]indazol-3,4,5(2H)-trione;
2-isopropyl-3-methoxy-2H-benzo[g]indazole-4,5-dione;
2-methyl-1-phenyl-1H-benzo[g]indazole-3,4,5(2H)-trione;
3-methoxy-1-phenyl-1H-benzo[g]indazol-4,5-dione;
2-ethyl-1-phenyl-1H-benzo[g]indazol-3,4,5(2H)-trione;
3-ethoxy-1-phenyl-1H-benzo[g]indazol-4,5-dione;
2-isobutyl-1-phenyl-1H-benzo[g]indazol-3,4,5(2H)-trione;
3-isobutoxy-1-phenyl-1H-benzo[g]indazol-4,5-dione;
2-isopentyl-1-phenyl-1H-benzo[g]indazol-3,4,5(2H)-trione;
3-(isopentyloxy)-1-phenyl-1H-benzo[g]indazol-4,5-dione;
2-isopropyl-1-phenyl-1H-benzo[g]indazol-3,4,5(2H)-trione;
2-methyl-3-phenyl-2,3-dihydro-1H-benzo[e]indazol-1,4,5-trione;
1-methoxy-3-phenyl-3H-benzo[e]indazol-4,5-dione;
1-isopropyl-2-methyl-1H-benzo[g]indazol-3,4,5(2H)-trione;
1-isopropyl-3-methoxy-1H-benzo[g]indazol-4,5-dione;
3-methoxy-1-(4-(trifluoromethyl)phenyl)-1H-benzo[g]indazol-4,5-dione;
1-(4-fluorophenyl)-3-methoxy-1H-benzo[g]indazol-4,5-dione;
1-methyl-2-phenyl-1H-benzo[g]indazol-3,4,5(2H)-trione;
7-fluoro-2-methyl-1-phenyl-1H-benzo[g]indazol-3,4,5(2H)-trione;
7-fluoro-3-methoxy-1-phenyl-1H-benzo[g]indazol-4,5-dione;
3-methoxy-7-nitro-1-phenyl-1H-benzo[g]indazol-4,5-dione;
7-amino-3-methoxy-1-phenyl-1H-benzo[g]indazol-4,5-dione; and
7-bromo-3-methoxy-1-phenyl-1H-benzo[g]indazol-4,5-dione.

13. A compound of Chemical Formula 2:
Chemical Formula 2

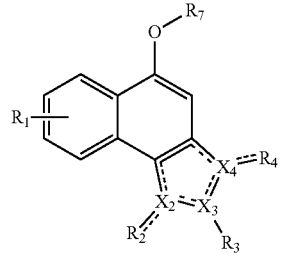

wherein:
$R_1$ is selected from the group consisting of H, $C_{1-6}$ alkyl, $C_{1-6}$ alkoxy, substituted or unsubstituted $C_{6-10}$ aryl, substituted or unsubstituted heteroaryl, halo, cyano, nitro and $NR_5R_6$;
$R_2$ and $R_3$ are each independently not present, or selected from the group consisting of H, O, $C_{1-6}$ alkyl, substituted or unsubstituted $C_{6-10}$ aryl and $C_{1-6}$ alkoxy; and
$R_4$ is selected from the group consisting of O, unsubstituted $C_{6-10}$ aryl and $C_{1-6}$ alkoxy, wherein at least one of $R_2$ and $R_4$ are O or $C_{1-6}$ alkoxy;
$R_5$ and $R_6$ are each independently H, $C_{1-6}$ alkyl or $C_{1-6}$ alkyl carbonyl, or $R_5$ and $R_6$ may be joined together to form a heterocyclyl containing at least one nitrogen atom in ring structure;
$R_7$ is $C_{1-6}$ alkyl, $C_{6-10}$ aryl-substituted $C_{1-6}$ alkyl, $C_{1-6}$ alkoxy-substituted $C_{1-6}$ alkyl, 5- or 6-membered heterocyclyl containing at least one hetero atom selected from the group consisting of N and O in ring structure, $C_{1-6}$ alkyl-substituted silyl and $C_{1-6}$ alkyl carbonyl;
$X_1$, $X_2$, $X_3$ and $X_4$ are each independently selected from C and N, wherein two of $X_1$, $X_2$, $X_3$ and $X_4$ are N, provided that $X_2$ and $X_4$ cannot simultaneously be N, and $X_1$ and $X_4$ cannot simultaneously be N;
≡≡≡ is a single bond or a double bond depending on $R_2$, $R_3$, $R_4$, $X_1$, $X_2$, $X_3$ and $X_4$;
wherein the alkyl is a linear, branched or cyclic alkyl, the heteroaryl is a 5- or 10-membered aromatic ring containing at least one hetero atom selected from the group consisting of N, O and S in the ring, and where the aryl or heteroaryl is substituted, a substituent thereof is $C_{1-6}$ alkyl, halo, or $C_{1-6}$ alkyl substituted with 1 to 3 halos.

14. The compound according to claim 13, selected from the group consisting of:
5-methoxy-1-phenyl-1H-benzo[g]indazol-3(2H)-one;
2-isopropyl-5-methoxy-1H-benzo[g]indazol-3(2H)-one;

5-methoxy-3-phenyl-2,3-dihydro-1H-benzo[e]indazol-1-one;
1-isopropyl-5-methoxy-1H-benzo[g]indazol-3(2H)-one;
5-methoxy-1-(4-(trifluoromethyl)phenyl)-1H-benzo[g]indazol-3(2H)-one;
1-(4-fluorophenyl)-5-methoxy-1H-benzo[g]indazol-3(2H)-one;
5-methoxy-2-phenyl-1H-benzo[g]indazol-3(2H)-one;
7-fluoro-5-methoxy-1-phenyl-1H-benzo[g]indazol-3(2H)-one;
5-methoxy-7-nitro-1-phenyl-1H-benzo[g]indazol-3(2H)-one;
7-bromo-5-methoxy-1-phenyl-1H-benzo[g]indazol-3(2H)-one;
5-(benzyloxy)-1-phenyl-1,2-dihydro-3H-benzo[g]indazol-3-one;
5-(methoxymethoxy)-1-phenyl-1,2-dihydro-3H-benzo[g]indazol-3-one;
1-phenyl-5-((tetrahydro-2H-pyran-2-yl)oxy)-1,2-dihydro-3H-benzo[g]indazol-3-one;
1-phenyl-5-((trimethylsilyl)oxy)-1,2-dihydro-3H-benzo[g]indazol-3-one; and
3-oxo-1-phenyl-2,3-dihydro-1H-benzo[g]indazol-5-yl acetate.

* * * * *